(12) United States Patent
Schmidt et al.

(10) Patent No.: US 7,888,005 B2
(45) Date of Patent: Feb. 15, 2011

(54) INHIBITORS OF MACROMOLECULAR ACTIVITY

(75) Inventors: Francis J. Schmidt, Columbia, MO (US); Farahnaz Rahmatpanah, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 683 days.

(21) Appl. No.: 10/248,735

(22) Filed: Feb. 13, 2003

(65) Prior Publication Data

US 2004/0170978 A1      Sep. 2, 2004

Related U.S. Application Data

(60) Provisional application No. 60/319,940, filed on Feb. 12, 2003.

(51) Int. Cl.
C12Q 1/68      (2006.01)
C12Q 1/18      (2006.01)

(52) U.S. Cl. .............................. 435/6; 435/32

(58) Field of Classification Search ............... 435/6, 435/197; 536/23.4, 23.1
See application file for complete search history.

(56) References Cited

FOREIGN PATENT DOCUMENTS

WO      WO 02/083837 A1 * 10/2002

OTHER PUBLICATIONS

Attwood, T. K. Science vol. 290, Oct. 20, 2000.*

* cited by examiner

*Primary Examiner*—Larry R. Helms
*Assistant Examiner*—Khatol Shahnan-Shah
(74) *Attorney, Agent, or Firm*—Mayer Brown LLP

(57) ABSTRACT

The present invention relates generally to methods, kits, compositions, and combinations to identify anti-infective or anti-pathogenic agents. The present invention also relates to methods, kits, compositions, and combinations directed to identifying elements of RNA metabolism related to pathogen propagation, monitoring of these RNA metabolic events, and to agents capable of interrupting RNA metabolism in a pathogen-specific fashion.

24 Claims, 6 Drawing Sheets

BACTERIAL PLATTING ASSAY FOR RNase P INHIBITION

INHIBITION OF E. COLI CONTAINING A SINGLE rnpA GENE

Fig. 3a

MeOH CRUDE EXTRACT OF *ARCTOSTAPHYLOSS GLAUCA*

| | | |
|---|---|---|
| WEIGHT (mg) | | 855.6 |
| INHIBITION* | RNase P | − + |
| 1000 μg/mL | | − ++++ |
| 500 μg/mL | | − + + |

POLYAMIDE 6S

| FRACTION | H₂O | MeOH/H₂O(1:1) | MeOH/CH₂Cl₂(4:1) | MeOH/CH₂Cl₂(1:1) | MeOH/NH₄OH(9:1) |
|---|---|---|---|---|---|
| WEIGHT (mg) | 333.4 | 157.3 | 58.4 | 37.5 | 233.4 |
| INHIBITION* RNase P (− +) | | | | | |
| 1000 μg/mL | − − | − ++++ | − ++++ | − + + | − ++ |
| 500 μg/mL | − − | − ++++ | − − | − + + | − ++ |
| 250 μg/mL | − − | − − | − − | − − | − + + |

| | | A | HP20SS (MeOH/H₂O) | | | |
|---|---|---|---|---|---|---|
| FRACTION | | 0:10 | 2:8 | 4:6 | 6:4 | 8:2 | 10:0 |
| WEIGHT (mg) | | 24.5 | 12.8 | 27.6 | 21.4 | 29.3 | 42.6 |
| INHIBITION* | RNase P | | | | | | |
| 1000 g/mL | −− | +++ | ++++ | ++++ | ++++ | +++ | +++ |
| | + | −−− | ++++ | ++++ | ++++ | −−− | −−− |
| 500 g/mL | −− | ++ | ++++ | ++++ | ++++ | +++ | +++ |
| | + | −−− | −−− | −−− | −−− | −−− | −−− |
| 250 g/mL | −− | ++ | ++++ | +++ | ++++ | ++ | + |
| | + | −−− | −−− | −−− | −−− | −−− | −−− |
| 125 g/mL | −− | + | ++++ | ++ | ++++ | + | −−− |
| | + | −−− | −−− | −−− | −−− | −−− | −−− |
| 63 g/mL | −− | −−− | +++ | + | +++ | −−− | −−− |
| | + | −−− | −−− | −−− | −−− | −−− | −−− |
| 32 g/mL | −− | −−− | +++ | −−− | ++ | −−− | −−− |
| | + | −−− | −−− | −−− | −−− | −−− | −−− |

HPLC (C$_{18}$ MeCN/H$_2$O)

| FRACTION | | 1 | 2 | 3 | 4 | 5 | 6 |
|---|---|---|---|---|---|---|---|
| WEIGHT (mg) | | 4.8 | 0.9 | 1.2 | 2.5 | 1.7 | 0.8 |
| INHIBITION* | RNase P | | | | | | |
| 200 g/mL | − | --- | +++ | +++ | --- | ++++ | +++ |
|  | + | --- | +++ | +++ | --- | ++++ | + |
| 100 g/mL | − | --- | ++ | +++ | --- | ++++ | +++ |
|  | + | --- | --- | + | --- | + | + |
| 50 g/mL | − | --- | --- | ++ | --- | +++ | ++ |
|  | + | --- | --- | --- | --- | --- | --- |
| 25 g/mL | − | --- | --- | + | --- | ++ | --- |
|  | + | --- | --- | --- | --- | --- | --- |
| 13 g/mL | − | --- | --- | --- | --- | ++ | --- |
|  | + | --- | --- | --- | --- | --- | --- |

JD-P-I-40-3 (GALLIC ACID) — fraction 3

JD-P-I-40-5 (3-O-GALLOYLSHIKIMIC ACID) — fraction 5

Fig. 3d

|  |  |  |  |  | C |  |  |  |  |
|---|---|---|---|---|---|---|---|---|---|
|  |  |  |  |  | HPLC ($C_{18}$ MeCN/$H_2O$) | | | | |
| FRACTION | 1 | 2 | 3 | 4 | 5 | 6 | 7 | 8 | 9 |
| WEIGHT (mg) | 8.2 | 0.1 | 4.5 | 1.2 | 0.3 | 1.8 | 1.9 | 0.1 | 7.3 |
| INHIBITION* RNase P | | | | | | | | | |
| 200 g/mL    − | + | nt | + | ++ | ++++ | ++++ | ++++ | nt | --- |
|             + | --- | --- | --- | --- | + | ++ | ++ | | --- |
| 100 g/mL    − | + | | --- | ++ | ++++ | ++++ | +++ | | --- |
|             + | --- | | --- | --- | --- | --- | --- | | --- |
| 50 g/mL     − | --- | | --- | + | ++ | +++ | ++ | | --- |
|             + | --- | | --- | --- | --- | --- | --- | | --- |
| 25 g/mL     − | --- | | --- | --- | ++ | ++ | ++ | | --- |
|             + | --- | | --- | --- | --- | --- | --- | | --- |
| 13 g/mL     − | --- | | --- | --- | --- | ++ | + | | --- |
|             + | --- | | --- | --- | --- | --- | --- | | --- |

JD-P-I-45-6 (fraction 6)   JD-P-I-45-7 (fraction 7)

INHIBITORS OF MACROMOLECULAR ACTIVITY

RELATED APPLICATIONS

This application claims priority from U.S. Provisional Patent Application Ser. No. U.S. 60/319,940 filed Feb. 12, 2003, which is hereby incorporated by reference.

BACKGROUND OF INVENTION

Pathogen induced infections in humans, animals, and tissue culture have generally been treated with anti-infective agents such as antibiotic, antimicrobial, antiviral or antifungal agents, depending on the type of pathogen involved. However, these agents have led to detrimental selection of pathogens that have become resistant to these administered agents. Today, infectious disease specialists now speak openly of a coming post-antibiotic era as previously well-controlled organisms have now become resistant to commonly available antibiotics. For example, *Staphylococcus aureus* is now widely resistant to methicillin. Methicillin-resistant *S. aureus* has been treated with vancomycin, however, the transfer of glycopeptide resistance from Enterococci into *S. aureus* species occurs readily in vivo, pointing to a short therapeutic life span of this drug. Although inappropriate use contributes to the rise in antibiotic resistance, it is also clear that resistant bacteria are selected when antibiotics are used prudently. Beyond this trend, opportunistic infections of bacterial, fungal and viral etiology have emerged in immunocompromised patients, especially in those infected by HIV.

The rise in antibiotic resistance can be slowed by changing patterns of antibiotic use or by using combination drug therapy. But it is also necessary to develop new anti-infective agents, as, for example, several microbes have been found to express multiple antibiotic resistance phenotypes which can be resistant to multiple treatment regimens and to antibiotics which are unrelated in chemical structure. The appearance of such bacteria and infections by such bacteria greatly increase the difficulty of identifying effective antibiotics and treating infections in humans or other animals, and in cell culture.

Although it is possible to use rational drug design to identify new anti-infective agents, the more common and fruitful strategy has been to screen large compound libraries for their activity against molecular targets. Recent efforts in combinatorial chemistry, combinatorial genetics and natural product chemistry address the need for larger libraries and for more efficient identification of active compounds. The expanding diversity of compounds for screening has not been matched by an equal expansion of targets. Current efforts in genomic sequencing are among the strategies being employed to identify new targets for screening.

Genomic sequence information is expected to lead to the identification of new targets for rational design of potential therapeutics. Thus, for example, genomic sequencing of pathogens' genomes has revealed widespread occurrence of "pathogenicity islands," that is, clusters of genes, likely spread through horizontal transmission, whose (often conditional) expression gives pathogenic ability to their bacterial host. The ability to pharmacologically intervene in this state would be extremely valuable. However, target identification can be the rate-limiting step in high-throughput screening, even with the extensive genomic information determined within the past five years. Although it is possible to identify targets based on well-characterized model biochemical and genetic systems, not all gene functions are known, even those of well-studied organisms. For example, no biochemical function has been assigned for 30% of open reading frames in the genome sequence of *Escherichia coli* (*E. coli*), the paradigm organism of molecular biology. One possible strategy for drug screening would start by fully determining the roles of these functions, however, the preliminary characterization required is labor-intensive and time-consuming.

A further paradigm for genome-driven pharmaceutical discovery is identifying inhibitors of lipid A synthesis. Extensive genetic studies identified lipid A synthesis as essential for growth, compounds were identified that inhibited galactose incorporation into bacteria, the target was identified as a unique deacetylase and the potency of the original compound was improved through a synthetic chemistry program.

Genomic information has the ability to streamline the search the extensive genetic studies that precede the screening and medicinal chemistry portions of a drug-discovery program. A promising approach is to identify genes on the basis of their phylogenetic conservation only. Phylogenetically conserved proteins, especially those that are conserved across all bacteria, for example, are likely more essential for microbial survival than genes that are either (1) unique to a few bacteria, or (2) common across all taxa. Neither of these assumptions has been rigorously tested, although Arigoni et al. (Arigoni F., et al., 1998. Nature Biotechnology 16:851-856) systematically tried to knock out 26 open reading frames of unknown function that are common to *E. coli* and *M genitalium*. Only six open reading frames were essential for growth in culture, as judged by the failure to recover the knockouts.

More recently, the open reading frames predicted from all known genomic sequences have been organized into Clusters of Orthologous Groups (COGs). The Clusters of Orthologous Group database is a tool in identifying molecular targets for screening. Orthologous protein sequences are derived from a common ancestor and appear in different species, as opposed to paralogues which arise from gene duplication within a species. The Clusters of Orthologous Group approach starts with BLAST comparison of all the open reading frames against all other open reading frames in the database, followed by classification of all the cross-species comparisons to identify those that appear in phylogenetically distinct species. Clusters of Orthologous Groups, therefore, represent the set of all phylogenetically conserved functions. The proteins within a single Clusters of Orthologous Group have related functions and very similar secondary structures.

One application of the Clusters of Orthologous Group database to yield new biochemical data has been published, see, Riley M. and Labedan B., 1997, Journal of Molecular Biology 268:857-868. The Clusters of Orthologous Group database was used to identify protein families that lack structurally characterized members. The structure of one of the proteins from a previously uncharacterized family was shown to have an alpha-beta plait topology, even though it does not exhibit any obvious sequence similarity to known members of this structural class.

Another such protein within the Cluster of Orthologous Group is ribonuclease P (COG0594). Prokaryotic ribonuclease P is a membrane-bound ribonucleoprotein ribozyme. Several antibiotics active against protein synthesis target ribonuclease P, but these compounds primarily target the ribosome and not ribonuclease P. For example, puromycin, the toxic-antibiotic that causes premature peptide chain termination inhibits the catalytic reaction of ribonuclease P RNA, albeit at a much higher concentration than required to inhibit protein synthesis (Vioque A., 1989. FEBS Letters 246:137-139). Neomycin B inhibits the action of *E. coli* ribonuclease P RNA at micromolar concentrations whether of not it is complexed with the protein subunit (Mikkelsen N. E., et al., 1990. PNAS 96:61 55-6160).

A limitation of these and similar informatics-based approaches is that the Orthologous Groups are not necessarily required for bacterial viability under laboratory conditions. For example, only eight of 26 genes identified by such an approach proved to be essential when the chromosome was disrupted at these loci. Furthermore, it is likely that many essential functions were missed in this analysis. Paralogous functions (those arising from gene duplications, and therefore represented more than once in a genome) are systematically excluded by such an approach. For example, the *E. coli* genome codes for paralogues of gyrA and gyrB. Search criteria that did not allow paralogues would exclude these as targets for drug discovery, despite the fact that they are targets for quinolines and novobiocin, respectively.

Resistance to an inhibitor can come about by amplification of the target which can titrate the effects of an inhibitor. While the original observation of the phenomenon depended on chromosomal mutation to increase the amount of the gene product, a multicopy situation is more easily realized by cloning the relevant function in a high-copy vector. This strategy has been used in analyses of several bacterial genes and operons, however, it appears not to have been widely used, if at all, for identifying targets for antimicrobials.

Published information regarding the use of bacterial genomics in the search for new anti-infectives has been confined mostly to cases where genomic information has been applied in a "top-down" fashion. Thus, individual genes have been targeted based on analysis of common distribution among genomes whose sequences are known.

The phenomenon of multicopy suppression identifies the targets for gene functions in the absence of detailed physiological, metabolic or genetic information. Multicopy suppression is widely used to genetically identify interacting macromolecules. Interacting molecules have been identified in yeast and bacteria, and multicopy suppression useful in identifying weakly interacting or poorly expressed molecules, see, for example, Hara H. et al., 1996. Microbial Drug Resistance 2:63-72. Also, see, Danese P N. et al., 1995. Journal of Bacteriology 177 (17):4969-73. For another example, see Ueguchi C. and Ito K 1992. Journal of Bacteriology 1 74:1454-61. Also see, Berg C M. et al., 1988. Gene 65(2): 195-202).

The RNA processing enzyme ribonuclease P is present in all cells and organelles that carry out tRNA biosynthesis. It cleaves the 5' end of precursor tRNA to generate the 5' end of mature tRNA in both prokaryotic and eukaryotic. In *Escherichia coli*, RNaseP was shown to participate in processing of rRNA precursors as well. RNaseP is unique among all the tRNA processing enzymes in having an RNA motif that is required for its function.

In all bacteria investigated thus far, it has been found that the enzyme is composed of two subunits, a small (about 14 kDa) protein and a large (about 130 kDa) RNA. The RNA subunit, RNaseP RNA, exhibits considerable variability in size among different species ranging from 140-490 nucleotides in length.

Previous work with *E. coli, Bacillus subtilis* and other bacteria showed that the RNA subunits from gram negative and positive bacteria can catalyze the cleavage of appropriate substrates in vitro, in buffers containing >20 mM $Mg^{+2}$. In other words, all of the specific catalytic residues required for the function of RNaseP reside in these RNA subunits.

Both monovalent ($K^+$ or $NH_4^+$) and divalent ($Mg^{2+}$ and $Ca^{2+}$) cations are of critical importance in the RNaseP reaction. Higher ionic strength than those which are optimal for the native ribozyme can suppress the affect of many mutations in the RNA only reaction, apparently by stabilizing the structure of RNA.

In addition to its structural role, $Mg^{2+}$ is proposed to promote catalysis by activating a water molecule to hydrolyze the susceptible phosphodiester bond in the substrate RNA and also coordinating on phosphate oxygens.

The stoichiometry of subunits in the holoenzyme is 1:1. The dissociation constant for the specific interactions of the subunits in the holoenzyme is about $4 \times 10^{-10}$ M. However the dissociation constant of $2 \times 10^{-8}$ to $6 \times 10^{-8}$ M was observed when C5 protein interacts with various RNA molecules in a nonmanner.

Mammals express multiple isoforms of RNaseP RNA (Li and Williams, 1995). Three novel genes encoding small RNAs homologous to human and mouse RNaseP RNA have been isolated from a mouse genomic library. In addition, similar short homologues of RNaseP are expressed in rate, rabbit and human cells.

The protein cofactor of RNaseP from *E. coli* (C5 protein) is a molecule of 119 amino acids, with a molecular mass of 13,700 daltons. Although this protein is identical in size to the C5 protein from the *B. subtilis* RNaseP (P-protein), there is only 25% homology between the primary sequence of the two proteins. In addition, both C5 and P-Proteins can be mixed with the heterologous P and M1RNAs to form functional hybrid holoenzymes. In addition, diverse bacterial RNA's assemble with the protein subunit of *E. coli* and diverse protein subunits assemble with the RNA compound of *E. coli*. Therefore, RNaseP holoenzyme share common features in their assembly pathway.

The C5 protein moiety functions as an electrostatic shield that allows two negatively charged RNA molecules (the catalytic subunit and the substrate) to interact. Furthermore, the presence of the protein in vitro increases the rate of cleavage reaction by RNaseP holoenzyme 20 fold.

It has been shown that at high ionic strength the cleavage reaction is protein independent, but the enzymatic turnover is slow. One of the important affects of high salt concentration is to facilitate substrate binding in the absence of protein probably by decreasing the repulsion between polyanionic enzyme and substrate RNAs. In addition to its function as a counter ion, the protein subunit facilitates substrate binding without interfering with rapid product release. In addition the protein subunit can stabilize the structure of RNA and thereby suppress the affect of many mutations that affect the RNA only reaction.

To understand the function of RNaseP it is important to elucidate how this enzyme recognizes its substrate. It is known that the tertiary folding of tRNA moiety of tRNA precursor molecule plays an important role in the enzyme substrate recognition.

The holoenzyme (RNaseP) binds to the helix formed by coaxial stacking of the common arm and acceptor stem of the tRNA, which is adjacent to the side of cleavage. In addition, the RNaseP holoenzyme recognizes the mature domain of precursor tRNA.

Work accomplished by Talbot and Altman (1994) revealed that regions of M1 RNA that interact with C5 proteins are clustered into three main areas that are localized between nucleotides 41-99, 168-198 and 266-287. Some point mutations that significantly affect the activity of M1RNA are located in these regions. Furthermore, nucleotides 254-259 and 291-195 form a binding site for a magnesium ion. The $Mg^{2+}$ ion bound in this vicinity participates in the chemical step of the cleavage reaction.

Many mutants defective in RNaseP have been isolated. These mutants seem to fall into two groups. One of these two groups is exemplified by the rnpA 49 mutation. The rnpA 49 mutation in the rnpA gene, the gene coding for C5 protein in *E. coli* results in an arginine to histidine alteration at position 46 in the C5 protein.

Apirion (1979) found that rnpA 49 is a recessive point mutation. Apirion and Watson (1979) analyzed a second class of mutation (rnpB, gene coding for M1RNA) which affects the RNaseP function. This temperature sensitive mutation carried by the rnpB strain is located between min 64 and min 81 of the *E. coli* chromosome. It has been shown that the rnpA and rnpB mutation occurs in two different genes (Apirion and Watson, 1979).

Cells bearing the rnpA 49 mutation are not able to grow at non-permissive temperature (42° C.). The tRNA precursor is accumulated when these cells shifted from permissive temperature to non-permissive perature (Schedl, et al., 1975). In addition, nonRNa-functional seP can be characterized by the appearance of a 19S RNA molecule, which contains 16S rRNA and spacer tRNA, and of a number of tRNA precursor molecules, and by the disappearance of the 4.5 SRNA molecule. Work from this laboratory showed that the over expression of the rnpB gene (gene coding the RNA subunit) from a high copy vector can complement or suppress the temperature sensitive phenotype of *E. coli* strain bearing rnpA 49.

Baer, et al. (1989) found that the temperature sensitive phenotype of cell bearing the A49 mutation can be suppressed by increasing in the efficiency of assembly of the holoenzyme in vivo. Moreover, in the presence of excess M1RNA the cleavage activity of reconstituted holoenzyme from wild type M1RNA and $C5^{A49}$ increases in vitro as well as in vivo (Baer, et al., 1989). (Baer et al., 1989) also found that the Arg-46 to His-46 mutation in the $C5^{A49}$ protein affects the ability of the protein to participate with M1RNA in the normal assembly process of RNaseP.

In addition, a study by Morse & Schmidt (1993) showed that the catalytic activity of different RNA's mutant (M1RNA) are similar to wild type RNA. However, strains of *E. coli* bearing these mutations cannot support cell growth in vivo which indicates that some steps other than catalysis must be responsible for the loss of biological function in vivo. Several experiments have suggested that assembly of RNaseP is deficient in these mutants. Thus the assembly of the RNA moiety and C5 protein is required for cell growth.

Therefore, it would be highly advantageous to identify anti-infective agents through high-throughput screening and then to use the sequences identified through a multicopy suppression assay to define targets and, potentially, modes of resistance and compounds directed to these targets. Each such identified target can then be used in an iterative fashion to classify similar agents at an early stage of development, direct further searches for lead compounds that are focused on one or more defined targets, and identify agents that are likely to be compromised by known means of resistance, for example, drug efflux pumps. It would also be highly advantageous to have an assay that allows screens that can be directed to a novel target, that can be used to identify inhibitors of pathogenic components, that can be used in cases were cell viability depends on assembly, that can be extended to other targets, such as sensory, secretory, and regulatory bacterial macromolecular assemblies, and/or that can be used as a high throughput screening assay for inhibitors of macromolecular assembly.

FIELD OF THE INVENTION

The present invention relates generally to methods, kits, compositions, and combinations to identify anti-infective or anti-pathogenic agents. The present invention also relates to methods, kits, compositions, and combinations directed to identifying elements of RNA metabolism related to pathogen propagation, monitoring of these RNA metabolic events, and to agents capable of interrupting RNA metabolism in a pathogen-specific fashion.

SUMMARY OF INVENTION

The present invention is directed to methods, kits, compositions, and combinations to identify anti-infective and/or anti-pathogenic agents. In one embodiment of the present invention, a method for identifying a pathogen-inhibiting agent that selectively interrupts assembly of a predetermined biological process is provided. The method comprises contacting a genetically engineered host cell that contains a sequence encoding a predetermined biological process operatively associated with a regulatory sequence that controls gene expression (so that the predetermined biological process gene product is stably expressed by the host cell) with a pathogen-inhibiting agent for a predetermined amount of time; and measuring the growth of the host cell containing the sequence over time. The amount of growth that occurs in this host cell containing the sequence is compared to the growth of a host cell genetically engineered to contain multiple sequences encoding the predetermined biological process and operatively associated with a regulatory sequence that controls gene expression after being contacted with the pathogen-inhibiting agent for a predetermined amount of time. A pathogen-inhibiting agent is identified (that is, a "hit" in an assay) by its ability to selectively inhibit the growth of the host cell containing the sequence, but not inhibit the growth of the host cell containing multicopy sequences. The order in which the growth is determined of the host cell containing either the sequence or the multicopy sequences is not narrowly critical.

Also included in the present invention is a method for identifying in a test sample an unknown pathogen-inhibiting agent that interrupts assembly of a predetermined biological process. The method comprises contacting a first bacterial strain containing a gene for the assembly of the predetermined biological process with the test sample; incubating the bacterial strain in presence of the test sample for a predetermined amount of time; measuring bacterial growth of the bacterial strain; contacting a second bacterial strain containing multiple copies of the gene for the assembly of the predetermined biological process with the test sample; incubating the bacterial strain in the presence of the test sample for a predetermined amount of time; measuring bacterial growth of the second bacterial strain of; and identifying the test sample that inhibits the growth of the first bacterial strain and does not inhibit the growth of the later bacterial strain.

The present invention also provides a method for treating a bacterial infection in a subject. The method comprises administering to the subject a therapeutically effective amount of a pathogen-inhibiting agent identified by the present method that interrupts assembly of a predetermined biological process, wherein the activity of the compound does not result in significant toxic side effects in the subject.

A method for selectively interrupting assembly of a predetermined bacterial biological process in a subject is also provided by the present invention. The method comprises administering to the subject a pathogen-inhibiting agent that selectively interrupts the assembly of a predetermined bacterial biological process, wherein the ability of the pathogen-inhibiting agent to selectively interrupt the assembly of the predetermined bacterial biological process is determined by contacting a first bacterial strain containing a gene for the assembly of the predetermined biological process with the pathogen-inhibiting agent; incubating the bacterial strain in presence of the pathogen-inhibiting agent for a predetermined amount of time; measuring bacterial growth of the bacterial strain; contacting a second bacterial strain containing multiple copies of the gene for the assembly of the predetermined biological process with the pathogen-inhibiting agent; incubating the second bacterial strain in the presence of the pathogen-inhibiting agent for a predetermined amount of time; measuring bacterial growth of the second bacterial strain; and identifying the pathogen-inhibiting agent that inhibits the growth of the first bacterial strain and does not inhibit the growth of the second bacterial strain.

BRIEF DESCRIPTION OF DRAWINGS

FIGS. 3(*a*) through 3(*d*) illustrate a typical fractionation procedure for extract 294-4 (*Arctostaphylos glauca*) ("--" RNase P: *E. coli* strain containing only one copy of rnp B (SURE 100); "+" RNase P: *E. coli* strain containing multiple copies of rnp B (SURE 46); "++++," very strong inhibition; "+++," strong; "++," middle strong, "+," weak; "---," no inhibition; "nt," not tested).

DETAILED DESCRIPTION

Figure 1:
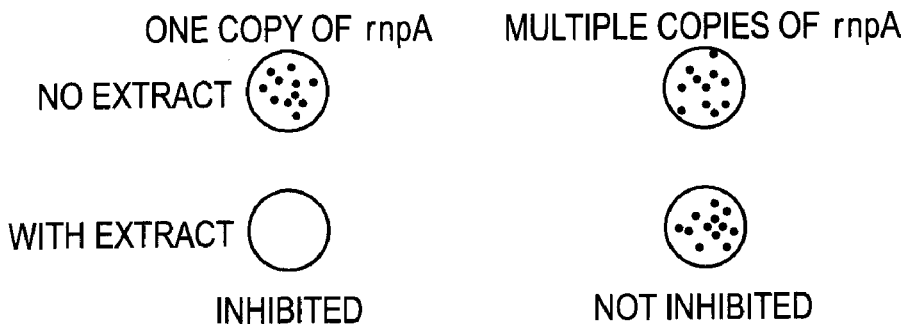
FIG. 1 is an illustrative bacterial platting assay for ribonuclease P inhibiting agents.
Figure 2:
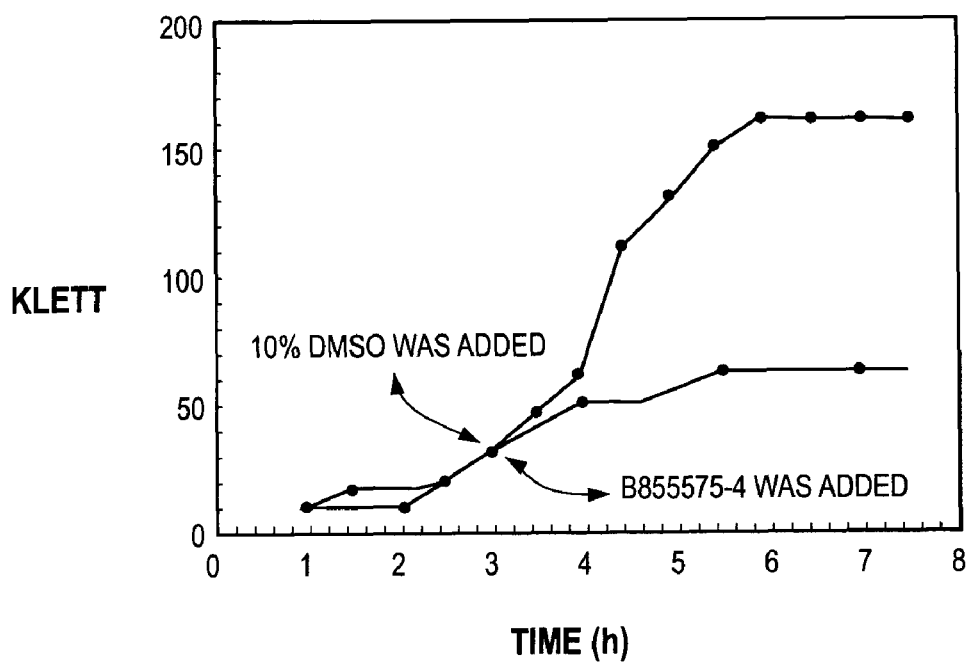
FIG. 2 shows inhibition of *E. coli* DM100 (containing a single rnp A gene) in liquid culture by test sample B855575-4 over a time period of approximately 8 hours.

While the present invention may be embodied in many different forms, several specific embodiments are discussed herein with the understanding that the present disclosure is to be considered only as an exemplification of the principles of the invention, and it is not intended to limit the invention to the embodiments illustrated. Where the invention is illustrated herein with particular reference to interruption of the assembly of ribonuclease P(COG0594), it will be understood that any other predetermined biological process can, if desired, be substituted in whole or in part for the assembly of ribonuclease P(COG0594) in the present invention herein described. Where the invention is illustrated herein with particular reference to a bacterial gene family, it will be understood that any other pathogen gene family, for example, viral or fungal, can, if desired, be substituted in whole or in part for the bacterial gene family in the present invention herein described.

The present invention is directed to methods, kits, compositions, and combinations to identify anti-infective or anti-pathogenic agents. In one embodiment of the present invention, a method for identifying a pathogen-inhibiting agent that selectively interrupts assembly of a predetermined biological process is provided. The method comprises contacting a genetically engineered host cell that contains a sequence encoding a predetermined biological process operatively associated with a regulatory sequence that controls gene expression (so that the predetermined biological process gene product is stably expressed by the host cell) with a pathogen-inhibiting agent for a predetermined amount of time; and measuring the growth of the host cell containing the sequence over time. The amount of growth that occurs in this host cell containing the single sequence is compared to the growth of a host cell genetically engineered to contain multiple sequences encoding the predetermined biological process and operatively associated with a regulatory sequence that controls gene expression (so that the predetermined biological process gene products are stably expressed by the host cell) after being contacted with the pathogen-inhibiting agent for a predetermined amount of time. A pathogen-inhibiting agent is identified (that is, a "hit" in an assay) by its ability to selectively inhibit the growth of the host cell containing the sequence, but not inhibit the growth of the host cell containing multiple sequences. The order in which the growth is determined of the host cell containing either the single sequence or the multiple sequences is not narrowly critical.

In another embodiment of the present invention, the methods, kits, compositions, and combinations are directed to identifying elements of RNA metabolism related to pathogen propagation. In another embodiment of the present invention, the methods, kits, compositions, and combinations are directed to the monitoring of these RNA metabolic events. In yet another embodiment, the present invention relates to the identification and use of agents capable of interrupting RNA metabolism in a pathogen-specific fashion.

In another embodiment of the present invention, the host cell containing the sequence can contain one or more sequences encoding a predetermined biological process, but in a multiple less than the number of sequences contained by the host cell genetically engineered to contain multiple sequences. For example, the host cell containing multiple sequences can have about 2 to about 10,000 times the number of sequences compared to the host cell containing the sequence. Illustratively, the host cell encoding multiple sequences will have about 2, 3, 10, 20, 50, 100, 200, 300, 400, 500, 1,000, 2,500, 5,000 or 10,000 times the number of sequences compared to the host cell containing the sequence. The multiple that is used is not narrowly critical as long as the growth of the two host cells can be compared and pathogen-inhibiting agents can be identified that inhibit the growth of the host cell encoding the one or more sequences encoding a predetermined biological process; while not inhibiting the growth of the host cell containing multiple sequences. Positive controls can be used to determine the multiple that provides the appropriate sensitivity for each assay condition.

The present invention is also directed to methods, kits, compositions, and combinations for detecting compounds (that is, a "hit") targeting pathogen functions by their ability to inhibit growth of wild-type pathogens but not of otherwise isogenic strains that overexpress these functions from a high-copy plasmid. In one embodiment, the methods of detecting compounds with such activity comprise: (1) screening large compound libraries for inhibitors of a pathogen, for example, a bacteria, fungi, or virus, on complex and minimal media; (2) identifying clones from a high-copy recombinant DNA library that are able to grow in the presence of the inhibitor; (3) rapidly screening positive clones, and identifying genes that confer resistance by reference to public genomic information; and (4) using the resistance-conferring high-copy plasmids as a "mini-library" to rapidly classify functions targeted by new "hits" from the library.

Although not wishing to be bound by theory, it is contemplated that three classes of gene functions will be identified in Steps 1-3 above. One class can be identified by a gene product whose essential function is inhibited by the extract and restored by overexpression of the gene product from a multicopy plasmid (Class 1). This class could include, for example, gene functions inhibited by antimetabolites. For this class target, the sequences would have the location in the genome, corresponding to the location of the gene specifying the target. A second class can be identified by a gene product whose essential function is inhibited by the extract and restored by overexpression of a gene product that interacts with the inhibited gene product (Class 2). This class includes, for example, the separate functions involved in ribonuclease P activity. Genetic studies indicate that overexpression of the RNA component of ribonuclease P suppresses mutations in the protein component, or it might include a two-component regulatory system. Two (or possibly more) sequences could be identified. These might be either closely linked, for example, in an operon, or relatively distant from each other. The third class can be identified by a gene product whose essential function is inhibited by the extract and restored by the overexpression of another, noninteracting macromolecule that reduces the intracellular concentration of the inhibitor to a level compatible with survival (Class 3). Examples of this mechanism could include efflux pumps and drug-binding proteins. This class occurs when several inhibitory extracts differing in their primary site of action are overcome by a single overexpressed gene product. It is contemplated, for example, that this product can be closely related to a known efflux pump multidrug resistance (MDR-type) protein.

It is also contemplated that overexpression of a specific binding protein that merely sequesters the inhibitory compound would be difficult to distinguish on its face from Class 1 or 2 events. It is possible, however, to make this distinction in cases where the target functions are known or can be inferred. For example, the effects of an antimetabolite would likely be overcome by high-copy expression of either the target itself, or of another molecule that could be identified as part of the same pathway. Functions that are clearly not related to the target pathway would be tentatively classified as binding molecules. More exact determination of the mechanism can be obtained by examining the pattern of resistance against closely related molecules or against molecules that target the same pathway. In the former case, a binding function would confer resistance against closely related compounds but not against molecules that target other steps in the same pathway. Conversely, a resistance function that was previously not known to interact with a pathway would likely overcome molecules that target several steps of a pathway.

In the above strategy, targets can be missed in several different scenarios, including, firstly, if the targets are naturally overexpressed in the pathogen under the experimental conditions. For example, in bacteria, the sequences of bacterial ribosomal RNA molecules are present on multiple copies in *E. coli*. Expression of rRNAs from a high-copy plasmid may not overcome an antibiotic, for example, aminoglycoside, that target the intact ribosome. Secondly, a gene may be lethal when overexpressed. For example, nucleic-acid-binding proteins may be growth-inhibitory when expressed in high copy number. Thirdly, gene products may exert a dominant effect when only some but not all copies are inhibited.

It is also noted that not all anti-microbial compounds exert their effect on all bacteria. This can be addressed by assaying all "hits" against a small number of known gram-negative and gram-positive clinical isolates at an early stage of analysis. A wide-spectrum agent can be used, for example, an antibiotic of the aminoglycoside, beta-lactam, or macrolide class, as well as more specific agents.

In yet another embodiment of the present invention, the methods, kits, compositions, and combinations are directed to identifying compounds that interfere with the assembly of a macromolecular component, for example, the assembly of bacterial ribonuclease P, an enzyme involved in transfer RNA biosynthesis, in a pathogen-specific fashion. While not wishing to be bound by theory it is known that a mutation in the protein subunit of ribonuclease P can be suppressed by the RNA gene when the RNA gene is on a high-copy plasmid. See, for example, Motamedi, H., Lee, K., Nichols, L., and Schmidt, F J. (1982). An RNA species involved in *Escherichia coli* ribonuclease P activity: Gene Cloning and Effect on Transfer RNA Synthesis in vivo. J. Mol. Biol. 162, 535-550. Also see, for example, Baer M F, Wesolowski D, Altman S. 1989. Characterization in vitro of the defect in a temperature-sensitive mutant of the protein subunit of RNase P from *Escherichia coli*. Journal of Bacteriology. 171: 6862-6866.

In one embodiment of the present invention, the methods, kits, compositions, and combinations are related to a multi-copy suppression screening assay in which, for example, a high concentration of RNA drives the assembly of the physiologically active holoenzyme, that is, a complete enzyme with an apoenzyme plus coenzyme, by mass action. In one embodiment of the present invention, the active holoenzyme has a mutation in a protein subunit, for example, ribonuclease P, that is suppressed by the RNA gene on a high-copy plasmid. This multicopy suppression results in the ability of the high concentration of RNA to drive the assembly of the physiologically active holoenzyme by mass action. In assaying for anti-infective or anti-pathogenic agents, those with activity subject to multicopy suppression, for example, by a cloned ribonuclease P RNA gene, can target the assembly of the in vivo form of the enzyme. Multicopy suppression can, for example, identify targets for gene functions in the absence of detailed physiological, metabolic, or genetic information.

In one embodiment, the present invention relates to a rapid method of high-throughput screening for inhibiting agents of ribonuclease P assembly. In yet another embodiment, the present invention utilizes two matched strains of *E. coli*. One contains the ribonuclease P RNA gene (rnpB) (SEQ ID NO:1) cloned on a high-copy plasmid having the following sequence:

```
  1 gaagctgacc agacagtcgc cgcttcgtcg tcgtcctctt cgggggagac
 51 gggcggaggg gaggaaagtc cgggctccat agggcagggt gccaggtaac
101 gcctgggggg gaaacccacg accagtgcaa cagagagcaa accgccgatg
151 gcccgcgcaa gcgggatcag gtaagggtga aagggtgcgg taagagcgca
201 ccgcgcggct ggtaacagtc cgtggcacgg taaactccac ccggagcaag
251 gccaaatagg ggttcataag gtacggcccg tactgaaccc gggtaggctg
301 cttgagccag tgagcgattg ctggcctaga tgaatgactg tccacgacag
351 aacccggctt atcggtcagt ttcacct
```

This strain is designated strain A. The second strain (strain B) in FIGS. 3(a) through 3(d) contains the vector plasmid, but only a chromosomal copy of rnpB (SEQ ID NO:1). Potential antimicrobials are identified from test compounds, which may be from, for example, compound libraries (such as natural products, combinatorial collections, etc.), and exposed to the matched E. coli strains. Because ribonuclease P assembly in strain A is favored by mass action (due to the excess synthesis of the RNA component), strain A will grow even in the presence of a ribonuclease P inhibitor. Strain B, with a single chromosomal copy of the ribonuclease P gene, will not be able to grow in the presence of a ribonuclease P inhibitor. If strain A grows but strain B does not, the test compound is a presumptive inhibitor of ribonuclease P assembly.

Besides being useful for human treatment and treatment of cell cultures, the present invention is also useful for identifying agents for veterinary treatment of mammals, reptiles, birds, exotic animals and farm animals, including mammals, rodents, and the like. In one embodiment, the mammal includes a primate, for example, a human, monkey, or lemur, a horse, a dog, a pig, or a cat. In another embodiment, the rodent includes a rat, a mouse, a squirrel or a guinea pig.

Included in the methods, kits, combinations and compositions of the present invention are the isomeric forms and tautomers of the described compounds and the pharmaceutically-acceptable salts thereof. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric and galacturonic acids.

Also included in the methods, kits, combinations and compositions of the present invention are prodrugs of the described compounds and the pharmaceutically-acceptable salts thereof. The term "prodrug" refers to a drug or compound in which the pharmacological action (active curative agent) results from conversion by metabolic processes within the body. Prodrugs are generally considered drug precursors that, following administration to a subject and subsequent absorption, are converted to an active or a more active species via some process, such as a metabolic process. Other products from the conversion process are easily disposed of by the body. Prodrugs typically produce products from the conversion process which are generally accepted as safe. Prodrugs generally have a chemical group present on the prodrug which renders it less active and/or confers solubility or some other property to the drug. Once the chemical group has been cleaved from the prodrug the more active drug is generated. Prodrugs may be designed as reversible drug derivatives and utilized as modifiers to enhance drug transport to site-specific tissues. The design of prodrugs to date has been to increase the effective water solubility of the therapeutic compound for targeting to regions where water is the principal solvent. Prodrugs are typically prepared by covalent attachment of a moiety, which results in a compound that is therapeutically inactive until modified by a metabolic system. For example, Fedorak, et al., Am. J. Physiol, 269:G210-218 (1995), describe dexamethasone-beta-D-glucuronide. McLoed, et al., Gastroenterol., 106:405-413 (1994), describe dexamethasone-succinate-dextrans. Hochhaus, et al., Biomed. Chrom., 6:283-286 (1992), describe dexamethasone-21-sulphobenzoate sodium and dexamethasone-21-isonicotinate. Additionally, J. Larsen and H. Bundgaard [Int. J. Pharmaceutics, 37, 87 (1987)] describe the evaluation of N-acylsulfonamides as potential prodrug derivatives. J. Larsen et al., [Int. J. Pharmaceutics, 47, 103 (1988)] describe the evaluation of N-methylsulfonamides as potential prodrug derivatives. Prodrugs are also described in, for example, Sinkula et al., J. Pharm. Sci., 64:181-210 (1975). Illustratively, this includes changes such as the acetylation of phenolic hydroxyl groups, which affords, for example, a prodrug with potentially improved formulation and delivery characteristics, including, for example, improved bioavailability and other pharmacodynamic parameters.

The term "derivative" refers to a compound that is produced from another compound of similar structure by the replacement of substitution of one atom, molecule or group by another. For example, a hydrogen atom of a compound may be substituted by alkyl, acyl, amino, etc., to produce a derivative of that compound.

Furthermore, once a pathogen-inhibiting agent has been identified using the present invention, it may be modified in a variety of ways, including by conventional chemical, physical, and biochemical means, to enhance its efficacy, stability, pharmaceutical compatibility, and the like. Such modified compounds possessing anti-pathogenic activity or their prodrugs, are also included in the present invention.

The pathogen-inhibiting agents of the present invention may be administered, if desired, in the form of a salt, an ester, an amide, an enantiomer, an isomer, a tautomer, a prodrug, a derivative or the like, provided the salt, ester, amide, enantiomer, isomer, tautomer, prodrug, or derivative is suitable pharmacologically, that is, effective in the present methods, kits, combinations, and compositions. Salts, esters, amides, enantiomers, isomers, tautomers, prodrugs and other derivatives of the active agents may be prepared using standard procedures known to those skilled in the art of synthetic organic chemistry and described, for example, by M. B. Smith and J. March, Advanced Organic Chemistry; Reactions, Mechanisms and Structure, 5th Ed. (New York: Wiley-Interscience, 2001). For example, acid addition salts are prepared from the free base using conventional methodology, and involve reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, for example, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, for example, hydrochloric acid, hydrobromic acid, sulfuric acid, nitric acid, phosphoric acid, and the like. An acid addition salt may be reconverted to the free base by treatment with a suitable base. Illustratively, acid addition salts of the active agents include, for example, halide salts, such as may be prepared using hydrochloric or hydrobromic acids; basic salts include, for example, alkali metal salts the sodium salt, and copper salts. Preparation of esters involves functionalization of hydroxyl and/or carboxyl groups which may be present within the molecular structure of the drug. The esters are typically acyl-substituted derivatives of free alcohol groups, that is, moieties that are derived from carboxylic acids of the formula RCOOH where R is alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

The pathogen-inhibiting agents of the present invention can be formulated as a single pharmaceutical composition containing at least one pathogen-inhibiting agent or as independent multiple pharmaceutical compositions where each composition contains at least one pathogen-inhibiting agent.

Toxicity and therapeutic efficacy of the pathogen-inhibiting agents of the present invention can be determined by standard pharmaceutical procedures, for example, for determining $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

It is understood that specific dose levels of the pathogen-inhibiting agents of the present invention for any particular subject depends upon a variety of factors including the type of subject, for example, a human, a mammal, etc., the activity of the specific agent employed, the age, body weight, general health, sex, and diet of the subject, the time of administration, the rate of excretion, the drug combination, if any, and the severity of the particular disease being treated and the form of administration.

Treatment dosages generally may be titrated to optimize safety and efficacy. Typically, dosage-effect relationships from in vitro studies initially can provide useful guidance on the proper doses for patient administration. Studies in animal models also generally may be used for guidance regarding effective dosages for treatment of a particular disease in accordance with the present invention. In terms of treatment protocols, it should be appreciated that the dosage to be administered will depend on several factors, including the particular agent that is administered, the route administered, the condition of the particular subject, etc. Generally speaking, one will desire to administer an amount of the compound that is effective to achieve a serum level commensurate with the concentrations found to be effective in vitro. Thus, where a compound is found to demonstrate in vitro activity at, for example, 10 µM, one will desire to administer an amount of the drug that is effective to provide at least about a 10 µM concentration in vivo in the subject. Determination of these parameters are well within the skill of the art.

These considerations, as well as effective formulations and administration procedures are well known in the art and are described in standard textbooks.

An "anti-infective effective amount" or "anti-pathogenic effective amount" is intended to qualify the amount of a pathogen-inhibiting agent required to treat, prevent or relieve to some extent one or more of the symptoms of an infectious or pathogenic disease or disorder, including, but is not limited to: 1) reduction in the number of pathogenic cells either in vitro or in vitro; 2) inhibition (that is, slowing to some extent, or stopping) of pathogen cell infiltration into unaffected cells; 3) inhibition (that is, slowing to some extent, or stopping) of pathogen cell infiltration into peripheral organs; 4) inhibition, to some extent, of pathogen cell growth; and/or 5) relieving or reducing to some extent one or more of the symptoms associated with the infectious or pathogenic disease or disorder.

The phrase "combination therapy" (or "co-therapy") embraces the administration of a pathogen-inhibiting agent of the present invention and another pharmaceutical agent, including, for example, an anti-infective agent such as an antibiotic, antimicrobial, antiviral or antifungal agents, depending on the type of pathogen being treated, as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single tablets or capsules for each of the therapeutic agents. Sequential or substantially simultaneous administration of each therapeutic agent can be effected by any appropriate route including, but not limited to, oral routes, intravenous routes, intramuscular routes, percutaneous routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all-therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, an anti-neoplastic agent, an immunosuppressant agent, or an immunomodulator) and non-drug therapies (such as, but not limited to, surgery or radiation treatment).

Antibacterial agents that can be used in combination with a pathogen-inhibiting agent of the present invention include, but are not limited to: (1) aminoglycosides, including, amikacin, arbekacin, bambermycins, butirosin, dibekacin, dihydrostreptomycin, fortimicins, gentamicin, Isepamicin, kanamycin, micronomicin, neomycin, netilmicin, paromomycin, ribostamycin, sisomicin, spectinomycin, streptomycin, tobramycin, and trospectomycin; (2) amphenicols, including, azidamfenicol, chloramphenicol, and thiamphenicol; (3) ansamycins, including, rifamide, rifampin, rifamycin, rifapentine, and rifaximin; (4) beta-lactams; (5) carbacephems, including, Ioracarbef; (6) carbapenems, including biapenem, ertapenem, fropenem, Imipenem, meropenem, panipenem; (7) cephalosporins, including, cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefoselis, cefotaxime, cefotiam, cefozopran, cefpimizole, cefpiramide, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin C, cephalothin, cephapirin sodium, cephradine, and pivcefalexin; (8) cephamycins, including, cefbuperozone, cefmetazole, cefminox, cefotetan, and cefoxitin; (9) monobactams, including, aztreonam, carumonam, and tigemonam; (10) oxacephems, including, flomoxef, moxalactam; (11) penicillins, including, amdinocillin, amdinocillin pivoxil, amoxicillin, ampicillin, apalcillin, aspoxicillin, azidocillin, azlocillin, bacampicillin, carbenicillin, carindacillin, clometocillin, cloxacillin, cyclacillin, dicloxacillin, epicillin, fenbenicillin, floxacillin, hetacillin, lenampicillin, metampicillin, methicillin sodium, meziocillin, nafcillin, oxacillin, penamecillin, penethamate hydriodide, penicillin G, penicillin G benzathine, penicillin G procaine, penicillin N, penicillin O, penicillin V, penimepicycline, phenethicillin potassium, piperacillin, pivampicillin, propicillin, quinacillin, sulbenicillin, sultamicillin, talampicillin, temocillin, and ticarcillin; (12) ritipenem; (13) lincosamides, including, clindamycin, and lincomycin; (14) macrolides, including, azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, telithromycin, and troleandomycin; (15) polypeptides, including, amphomycin, bacitracin, bacitracin zinc, capreomycin, colistin, enduracidin, enviomycin, fusafungine, gramicidin, gramicidin S. polymyxin, quinupristin, ristocetin, teicoplanin, thiostrepton, tuberactinomycin, tyrocidine, tyrothricin, vancomycin, and viomycin; (16) tetracyclines, including, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, and tetracycline; (17) cycloserine; (18) dalfopristin; (19) mupirocin; (20) pristinamycin; (21) virginiamycin; (22) 2,4-diaminopyrimidines, including, brodimoprim, tetroxoprim, and trimethoprim; (23) nitrofurans, including, furaltadone, furazolium chloride, nifuratel, nifurfoline, nifurpirinol, nifurprazine, nifurtoinol, and nitrofurantoin; (24) oxazolidinones, including, linezolid; (25) quinolones and analogs, including, balofloxacin, cinoxacin, ciprofloxacin, clinafloxacin, enoxacin, fleroxacin, flumequine, gatifloxacin, gemifloxacin, grepafloxacin, lomefloxacin, miloxacin, moxifloxacin, nadifloxacin, nalidixic acid, norfloxacin, ofloxacin, oxolinic acid, pazufloxacin, pefloxacin, pipemidic acid, piromidic acid, rosoxacin, rufloxacin, sitafloxacin, sparfloxacin, tosufloxacin, and trovafloxacin; (26) sulfonamides, including, acetyl sulfamethoxypyrazine, chloramine-B, chloramine-T dichloramine T, $N^2$-formylsulfisomidine, $N^4$-beta-D-glucosylsulfanilamide, mafenide, noprylsulfamide, phthalylsulfacetamide, phthalylsulfathiazole, Salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanole, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $N^4$-sulfanilylsulfanilamide, sulfanilylurea, N-sulfanilyl-3,4-xylamide, sulfaperine, sulfaphenazole, sulfaproxyline, sulfapyrazine, sulfapyridine, sulfasomizole, sulfasymazine, sulfathiazole, sulfathiourea, sulfisomidine, and sulfisoxazole; (27) sulfones, including, acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, and thiazolsulfone; (28) clofoctol, hexedine; (29) methenamine; (30) metronidazole; (31) nitroxoline; (32) pexiganan; (33) taurolidine; (34) xibornol; (35) leprostatic, including, acedapsone, acetosulfone sodium, clofazimine, dapsone, diathymosulfone, glucosulfone sodium, hydnocarpic acid, solasulfone, succisulfone, and sulfoxone sodium; and (36) tuberculostatic, including, p-aminosalicylic acid, p-aminosalicylic acid hydrazide, benzoylpas, 5-bromosalicylhydroxamic aid, capreomycin, clofazimine, cyacetacide, cycloserine, dihydrostreptomycin, enviomycin, ethambutol, ethionamide, furonazide, glyconiazide, Isoniazid, morphazinamide, opiniazide, phenyl aminosalicylate, protionamide, pyrazinamide, rifabutin, rifalazil, rifampin, rifapentine, salinazid, streptomycin, streptonicozid, sulfoniazide, thiacetazone, tiocarlide, tuberactinomycin, tubercidin, and viomycin. Also, all the salts, esters, amides, enantiomers, isomers, tautomers, prodrugs and derivatives of these compounds, as well as combinations of the above mentioned antibacterial agents can be used in the methods, kits, combinations, and compositions herein described. (The Merck Index, $13^{th}$ Edition, Merck & Co. Rahway, N.J. (2001)).

Antifungal agents that can be used in combination with a pathogen-inhibiting agent of the present invention include, but are not limited to: (1) polyenes, including, amphotericin B, candicidin, dermostatin, filipin, fungichromin, hachimycin, hamycin, lucensomycin, mepartricin, natamycin, nystatin, pecilocin, and perimycin; (2) azaserine; (3) caspofungin; (4) griseofulvin (5) oligomycins; (6) pyrrolnitrin; (7) siccanin; (8) tubercidin; (9) viridin; (10) allylamines, including, butenafine, naftifine, and terbinafine; (11) imidazoles, including, bifonazole, butoconazole, chlordantoin, chlormidazole, cloconazole, clotrimazole, econazole, enilconazole, fenticonazole, flutrimazole, isoconazole, ketoconazole, lanoconazole, miconazole, neticonazole, omoconazole, oxiconazole nitrate, sertaconazole, sulconazole, and tioconazole; (12) thiocarbamates, including, liranaftate, tolciclate, tolindate, and tolnaftate; (13) triazoles, including, fluconazole, itraconazole, posaconazole, saperconazole, terconazole, and voriconazole; and (14) others, including, acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, hexetidine, loflucarban, nifuratel, potassium iodide, propionic acid, pyrithione, salicylanilide, sodium propionate, sulbentine, tenonitrozole, triacetin, undecylenic acid, and zinc propionate. Also, all the salts, esters, amides, enantiomers, isomers, tautomers, prodrugs and derivatives of these compounds, as well as combinations of the above mentioned antifungal agents can be used in the methods, kits, combinations, and compositions herein described. (The Merck Index, $13^{th}$ Edition, Merck & Co. Rahway, N.J. (2001)).

Antiviral agents that can be used in combination with a pathogen-inhibiting agent of the present invention include, but are not limited to: (1) monoclonal antibodies, including, palivizumab; (2) peptidomimetics, including, amprenavir, indinavir, lopinavir, nelfinavir, ritonavir, and saquinavir; (3) polynucleotides, including, ampligen, and fomivirsen; (4) purines and pyrimidinones, including, abacavir, acyclovir, adefovir, cidofovir, cytarabine, didanosine, dideoxyadenosine, edoxuydine, emtricitabine, famciclovir, floxuridine, ganciclovir, idoxuridine, inosine pranobex, lamivudine, MADU, penciclovir, sorivudine, stavudine, tenofovir, trifluridine, valacyclovir, valganciclovir, vidarabine, zalcitabine, and zidovudine; (5) sialic acid analogs, including, oseltamivir, and zanamivir; and (6) others, including, acemannan, acetylleucine monoethanolamine, amantadine, amidinomycin, atevirdine, capravirine, delavirdine, n-docosanol, efavirenz, foscarnet sodium, interferon-alpha, interferon-beta, interferon-gama, kethoxal, lysozyme, methisazone, moroxydine, nevirapine, pentafuside, pleconaril, podophyllotoxin, ribavirin, rimantadine, stallimycin, statolon, tremacamra, and tromantadine. Also, all the Salts, esters, amides, enantiomers, isomers, tautomers, prodrugs and derivatives of these compounds, as well as combinations of the above mentioned antiviral agents can be used in the methods, kits, combinations, and compositions herein described. (The Merck Index, 13$^{th}$ Edition, Merck & Co. Rahway, N.J. (2001)).

Classes of antineoplastic agents that can be used in combination with a pathogen-inhibiting agent of the present invention include, but are not limited to: (1) alkaloids; (2) alkylating agents; (3) antibiotics and analogs; (4) antimetabolites; (5) enzymes; (6) immunomodulators; (7) immunotoxins; (8) monoclonal antibodies; (9) platinum complexes; (10) hormonal, including, androgens, antiadrenals, antiandrogens, antiestrogens, antiprogestins, aromatase inhibitors, estrogens, LH-RH analogs, progestogens, retinoids, retinoid analogs, and somatostatin analogs; (11) photosensitizers; (12) radiation: (13) antimestatic agents; (14) chemomodulators; (15) chemosensitizers; (16) folic acid replenisher; (17) radiosensitizers; and (18) uroprotectives. Also, all the salts, esters, amides, enantiomers, isomers, tautomers, prodrugs and derivatives of these compounds, as well as combinations of the above antineoplastic agents can be used in the methods, kits, combinations, and compositions herein described. (The Merck Index, 13$^{th}$ Edition, Merck & Co. Rahway, N.J. (2001)).

An immunosuppressant agent that can be used in combination with a pathogen-inhibiting agent of the present invention include, but are not limited to: (1) alemtuzumab, (2) azathioprine, (3) basiliximab, (4) brequinar, (5) cyclosporin, (6) daclizumab, (7) 6-mercaptopurine, (8) mizoribine, (9) muromonab, (10) pimecrolimus, (11) rapamycin, and (12) tacrolimus. Also, all the salts, esters, amides, enantiomers, isomers, tautomers, prodrugs and derivatives of these compounds, as well as combinations of the above immunosuppressant agents can be used in the methods, kits, combinations, and compositions herein described. (The Merck Index, 13$^{th}$ Edition, Merck & Co. Rahway, N.J. (2001)).

An immunomodulator agent that can be used in combination with a pathogen-inhibiting agent of the present invention include, but are not limited to: (1) acemannan, (2) amiprilose, (3) ampligen, (4) bropirimine, (5) bucillamine, (6) ditiocarb sodium, (7) glatiramer, (8) imiquimod, (9) inosine pranobex, (10) interferon-beta, (11) interferon-gamma, (12) interleukin-2, (13) interleukin-10, (14) leflunomide, (15) lentinan, (16) levamisole, (17) lisofylline, (18) macrophage colony-stimulating factor, (19) mitoxantrone, (20) pidotimod, (21) platonin, (22) procodazole, (23) propagermanium, (24) romurtide, (25) thymomodulin, (26) thymopentin, and (27) ubenimex. Also, all the salts, esters, amides, enantiomers, isomers, tautomers, prodrugs and derivatives of these compounds, as well as combinations of the above immunomodulator agents can be used in the methods, kits, combinations, and compositions herein described. (The Merck Index, 13$^{th}$ Edition, Merck & Co. Rahway, N.J. (2001)).

The therapeutic compounds which make up a combination therapy may be in a combined dosage form or in separate dosage forms intended for substantially simultaneous administration. The therapeutic compounds that make up the combination therapy may also be administered sequentially, with either therapeutic compound being administered by a regimen calling for two step administration. Thus, a regimen may call for sequential administration of the therapeutic compounds with spaced-apart administration of the separate, active agents. The time period between the multiple administration steps may range from, for example, a few minutes to several hours to days, depending upon the properties of each therapeutic compound such as potency, solubility, bioavailability, plasma half-life and kinetic profile of the therapeutic compound, as well as depending upon the effect of food ingestion and the age and condition of the subject. Circadian variation of the target molecule concentration may also determine the optimal dose interval. The therapeutic compounds of the combined therapy whether administered simultaneously, substantially simultaneously, or sequentially, may involve a regimen calling for administration of one therapeutic compound by one route, for example, orally, and another therapeutic compound to be administered by the same or different route, for example, parenterally. Whether the therapeutic compounds of the combined therapy are administered orally, by inhalation spray, rectally, topically, buccally (for example, sublingual), or parenterally (for example, subcutaneous, intramuscular, intravenous and intradermal injections, or infusion techniques), separately or together, each such therapeutic compound will be contained in a suitable pharmaceutical formulation of pharmaceutically-acceptable excipients, diluents or other formulations components. Examples of drug formulations are discussed in, for example, Hoover, John E., Remington's Pharmaceutical Sciences, Mack Publishing Co., Easton, Pa., 1975. Another discussion of drug formulations can be found in Liberman, H. A. and Lachman, L., Eds., Pharmaceutical Dosage Forms, Marcel Decker, New York, N.Y., 1980.

In one embodiment of the present invention, an oral drug candidate fulfills two or more of the following criteria: (1) logP less than 5, (2) number of H-bond donors less than 5, (3) number of H-bond acceptors less than 10, and (4) $M_r$ less than 500. See, for example, Lipinski C A. 2000. J. Pharmacol. Toxicol. Meth. 44:235. Also see, for example, Clark D E. 1999. J. Pharm. Sci. 88:807. However, these criteria are not critical, as for example, antibiotics such as streptomycin and erythromycin fail to meet such criteria. Either specific intestinal transport mechanisms or chemical modification to promote absorption can overcome this difficulty. It is also noted that in one embodiment of the present invention, the test samples are screened to be active against whole cells. While not wishing to be bound by theory, this indicates that they are able to traverse the bacterial cell wall and membrane to reach their target.

In still another embodiment of the methods, kits, combinations, and compositions of the present invention, the pathogen-inhibiting agent is administered for treating, preventing, or reducing the risk of developing a pathogen induced disease or disorder in a subject by any means that produce contact of these compounds with their site of action in the body, for example in the ileum, the plasma, or the liver of a subject. For example the compositions can be administered, orally, rectally, bucally, percutaneously, intravenously, intramuscularly, or by direct absorption through mucous membrane tissue.

Additionally, the methods, kits, combinations, and compositions of the present invention may optionally include excipients, salts, emollients, stabilizers, antimicrobials, fragrances, and propellants.

In another embodiment of the present invention, the pathogen inhibiting agent comes in the form of a kit or package containing one or more therapeutic compounds. The therapeutic compounds of the present invention can be packaged in the form of a kit or package in which the hourly, daily, weekly, or monthly (or other periodic) dosages are arranged for proper sequential or simultaneous administration. The present invention further provides a kit or package containing a plurality of dosage units, adapted for successive daily administration, each dosage unit comprising at least one of the therapeutic compounds of the present invention. This drug delivery system can be used to facilitate administering any of the various embodiments of the therapeutic compounds of the present invention. In one embodiment, the system contains a plurality of dosages to be to be administered daily or weekly. The kit or package can also contain the agents utilized in combination therapy to facilitate proper administration of the dosage forms. The kits or packages also contain a set of instructions for the subject.

The term "pharmaceutically acceptable" is used adjectivally herein to mean that the modified noun is appropriate for use in a pharmaceutical product. Pharmaceutically acceptable cations include metallic ions and organic ions. More preferred metallic ions include, but are not limited to appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

"Therapeutic compound" means a compound or agent useful in the prophylaxis or treatment of a disease or disorder caused by a pathogen.

The term "pathogen" embraces any virus, microorganism, or other substance capable of causing a disease or disorder in an animal, including mammals, rodents, birds, or reptiles, and in cell culture. The term "virus" embraces DNA or RNA containing virus. The term "microorganism" embraces any microscopic organism of plant or animal origin and includes, for example, bacteria and fungi. The term "bacteria" refers to a broad class of prokaryotic microorganisms that typically multiplies by cell division, and generally have cell walls. Bacteria can be aerobic or anaerobic, motile or nonmotile, and may be free-living, saprophytic, parasitic or pathogenic. Fungi is a general term used to encompass both yeasts and molds. (See, for example, Stedman"s Medical-Dictionary, 25th Edition, Williams & Wilkins Eds. (1990)).

The term "anti-infective agent" or "anti-pathogenic agent" embraces an agent that inhibits or in some respects slows or stops the growth, propagation or replication of a pathogen. This includes, but is not limited to: 1) reducing the number of pathogenic cells in a subject or in cell culture; 2) inhibiting (that is, slowing to some extent or stopping) pathogen cell infiltration into unaffected cells; 3) inhibiting (that is, slowing to some extent or stopping) pathogen cell infiltration into peripheral organs; and/or 4) inhibiting to some extent or stopping pathogen cell growth, propagation or replication in vitro or in vivo. This includes an agent that interferes with assembly of a biochemical process, for example, the assembly of an enzyme, and can be involved in pathogen propagation or replication. According to the present invention, an anti-pathogenic agent can also be an agent that interferes with assembly anywhere on the RNA of a pathogen.

As used herein, the term "test sample" refers to a sample, comprising a compound, molecule, mixture, or complex, which is being tested for anti-pathogenic activity. In one embodiment the test sample is being tested for its ability to interfere with assembly of a biochemical process, for example, the assembly of an enzyme. The test sample can be virtually any agent, including without limitation metals, peptides, proteins, lipids, polysaccharides, small or large organic molecules, nucleotides (including non-naturally occurring nucleotides), and combinations thereof. Small organic molecules generally have a molecular weight of between about 50 daltons to about 2,500 daltons, and typically less than about 400 daltons. Complex mixtures of substances such as natural product extracts, which may include more than one potential anti-pathogenic agent, can also be tested, and the component that interferes with assembly of a biochemical process can be purified from the mixture in a subsequent step using standard fractionation and purification procedures known in the art.

Test samples may be derived from large libraries of synthetic or natural compounds. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or MycoSearch (N.C.), or are readily producible. Additionally, natural and synthetically produced libraries and compounds are readily modified through conventional chemical, physical, and biochemical means. For example, the compounds may be modified to enhance efficacy, stability, pharmaceutical compatibility, and the like.

As used herein, the term "assembly of a biological process" refers to the processes involved in the construction of a molecule required for its proper biological function. In one embodiment of the present invention, the biological process is involved in pathogen metabolism, propagation or replication. Illustratively, a biological process is RNA metabolism, and includes, for example, assembly of an enzyme such as, for example, the assembly of bacterial ribonuclease P. A biological process may be derived from any living organism, such as a vertebrate, particularly a mammal and even more particularly a human, or from a virus, bacterium, fungus, protozoan, parasite or bacteriophage. Target biological process may comprise wild type sequences, or, alternatively, mutant or variant sequences, including those with altered stability, activity, or other variant properties, or hybrid sequences to which heterologous sequences have been added. Furthermore, target biological process as used herein includes RNA that has been chemically modified, such as, for example, by conjugation of biotin, peptides, fluorescent molecules, and the like.

As used herein, the phrase "inhibition of host cell growth" refers to a reduction in the growth rate of a susceptible bacterial strain in the presence of an inhibitor. This reduction may be manifested as an inability to form single colonies on solid agar media, a diminished colony size on solid agar media, or as the diminution of the increase of biomass or the reduced production of a metabolic product, for example, acid, in liquid media, upon exposure to the inhibitory agent. The extent of reduction on exposure to the inhibitory agent may be complete (that is, no detectable growth occurs) or partial (for example, the rate of growth is reduced 10% or more).

In one embodiment of the present invention, the growth inhibition of the host cell, for example, a bacteria, is measured by adding the test sample and the genetically engineered host cell to media that supports the growth of the host cell. Illustratively, the mixture is incubated at 37° C. for a predetermined period of time, for example, 4, 6, 8, 12, 24, 36 or 48 hours, to allow the host cell the opportunity to reproduce or replicate and to allow for the interaction of the test sample with the host cell and the assembly of the biological process. Cell growth is, measured by, an increase in optical density at 640 nm of the culture; inhibition of cell growth is measured by a decrease in the optical density of the culture containing the test sample relative to that of a standard culture containing only the solvent in which the test sample is dissolved or suspended.

In yet another embodiment of the present invention, fractionation of a test sample is done by standard chromatographic techniques known in the art. In one embodiment of the present invention fractionation is performed by applying the sample to a solid phase extraction tube, such as, for example, a polyamide 6S column (for example, for extracting tannins, chlorophyll, humic acid, terpenoids, flavonoids, gallic acid, catechol A protocatechuic acid, and phloroglucinol from aqueous or methanol solutions), a polymerically bonded octadecyl (C18) bonded silica isolates column (for example, for purification of compounds from aqueous media), or a moderate carbon loading bonded silica (11% carbon) column (for example, for eluting hydrophobic compounds), and washing successively with polar and non-polar solvents and mixtures. In another embodiment of the present invention, fractionation of a test sample is performed by applying the sample to a HPLC column, such as, for example, a RP-amide column (for example, for retention and resolution of polar compounds), a $C_8$ column (for, example, for separation of basic and acidic compounds), a $C_{18}$ column (for example, for separation of basic and acidic analytes and separation of peptides and small proteins), or a cyano column (for example, for resolution of hydrophobic molecules), and exposing the test sample to various solvents to elute off the various analytes of the test sample. In yet another embodiment of the present invention fractionation of a test sample is performed by applying the sample to a Amberchrom® CG-300 or CG-1000 chromatographic grade resin column, or a Mitsubishi Diaion® SP20SS or HP20SS polymeric resin based styrene/divinylbenzene column. Optimization of eluting conditions to achieve appropriate resolution of a test sample are well known in the art and are described in standard textbooks and take into consideration, for example, the type of salt or solvent, the strength of the solvent or salt, buffer pH, ion pairing reagents used, temperature and column surface chemistry.

In another embodiment of the present invention, the methods of identifying pathogen-inhibiting agents that selectively interrupts assembly of a predetermined biological process are adapted to a high-throughput assay or screen. In one embodiment, the assays are carried out in commercially available polystyrene multiwell flat or round bottom sterile cell culture plates, see, for example, BD Falcon™ Multiwell Cell Culture Plates, with 6, 12, 24, 48, 96, 384, or 1536 wells.

In one embodiment of the present invention, the Clusters of Orthologous Group database was searched for biological assembly targets. The search included those that were simultaneously conserved in bacteria, mostly non-paralogous, and, where functions were known, are generally considered essential for macromolecular biosynthesis, see Table No. 1, below. While not wishing to be bound by theory, other targets contemplated could include components of regulatory processes, for example, protein kinases and DNA-binding proteins, components of DNA replication and repair pathways, components of bacterial cell wall, lipid, or lipoprotein synthesis pathways, or any other macromolecular component identified as a target of a growth-inhibitory agent.

TABLE NO 1

Identified COG's that are Likely Target Function

| Identification No. | Likely Target Function |
| --- | --- |
| COG0242 | N-formylmethionyl-tRNA deformylase |
| COG0858 | Ribosome-binding factor A |
| COG0264 | Translation elongation factor Ts |
| COG0290 | Translation initiation factor IF3 |
| COG0336 | tRNA-(guanine-N1) methyltransferase |
| COG0782 | Transcription elongation factor |
| COG0593 | ATPase involved in DNA replication initiation |
| COG0358 | DNA primase (bacterial type) |
| COG0587 | DNA-dependent DNA polymerase III alpha chain |
| COG0178 | Excinuclease ATPase subunit |
| COG0556 | Helicase subunit of the DNA excision repair complex |
| COG2255 | Helicase subunit of the Holliday junction resolvase (RuvB) |
| COG0632 | Holliday junction DNA helicase subunit |
| COG0272 | NAD-dependent DNA ligase (contains BRCT domain type II) |
| COG0322 | Nuclease subunit of the excinuclease complex |
| COG0594 | ribonuclease P protein component |
| COG0305 | Replicative DNA helicase |
| COG0544 | FKBP-type peptidyl-protyl cis-transisomerase (trigger factor) |
| COG0691 | tmRNA-binding protein SmpB |
| COG0275 | Predicted S-adenosylmethionine-dependent methyltransferase involved in cell envelope biogenesis |
| COG0682 | Prolipoprotein diacylglyceryltransferase |
| COG0597 | Lipoprotein signal peptidase |
| COG0653 | Preprotein translocase subunit SecA (ATPase, RNA helicase) |
| COG0690 | Preprotein translocase subunit SecF. |

TABLE NO 1-continued

Identified COG's that are Likely Target Function

| Identification No. | Likely Target Function |
|---|---|
| COG1136 | ABC-type (unclassified) transport system, ATPase component |
| COG0313 | Predicted methyltransferases |
| COG0319 | Uncharacterized BCR (putative metal-binding protein) |

Note that one identified target is the protein component of ribonuclease P (COG0594). Prokaryotic ribonuclease P is a membrane-bound ribonucleoprotein ribozyme. While not wishing to be bound by theory, it is believed that the metabolic function of prokaryotic ribonuclease P is to cleave transfer RNA precursors to produce the mature 5' end of the RNA. In contrast to other known ribozymes, ribonuclease P is catalytic in vivo: the RNA component carries out multiple rounds of catalysts.

While not wishing to be bound by theory, since transfer RNAs are required for all protein biosynthesis in the cell, it is contemplated that ribonuclease P is essential for growth. Bacterial mutants unable to assemble ribonuclease P at high temperature are also unable to grow at high temperature. Assembly of ribonuclease P in vivo involves two processes: (1) binding of the RNA and protein components to each other, and (2) the assembly of the ribonucleoprotein into a membrane-bound complex. The protein component plays a role in the binding of the complex to the inner bacterial membrane of E. coli.

Several laboratories have used genetic analysis and comparative sequence analysis to determine the basic features of ribonuclease P RNA required for function. Although the RNA is clearly essential for growth, the ribonuclease P RNA sequences are not closely conserved among different bacteria, rather, genetic analysis and comparative sequencing indicate that the overall secondary and tertiary structure of the RNA subunit is conserved among bacterial ribonuclease P RNAs. Consistent with this conclusion, it has been shown that ribonuclease P RNAs and proteins from many divergent bacteria can function in E. coli, binding to the E. coli protein or RNA component, respectively, to give a catalytically competent enzyme.

Data on the kinetic properties of ribonuclease P in vitro are consistent with the above observations obtained in vivo. The catalytic action of ribonuclease P seems to be relatively insensitive to perturbations in its primary structure. Thus, there are no absolutely essential catalytic residues, rather any small segment of ribonuclease P RNA can be deleted without totally abolishing in vitro catalytic activity. Furthermore, the in vitro catalytic properties of a number of mutant RNAs are identical to those of wild-type RNA. Since these mutant RNAs still cannot support bacterial growth, some step other than catalysis must be responsible for the loss of biological function in vivo. Several experiments show that assembly of ribonuclease P is deficient in these mutants.

Assembly of the ribonuclease P ribonucleoprotein complex in vitro seems to be relatively easily perturbed. Perturbation of RNA-protein assembly results in impaired cell growth, since mutational analysis has identified several mutations in both the protein and RNA subunits that affect either the association of the RNA and the protein subunits or the targeting of the complex to the membrane.

These considerations suggest that a drug discovery strategy directed toward assembly of the ribonuclease P complex rather than towards its catalytic function can be effective.

ribonuclease P is a two subunit ribozyme necessary for cell growth and survival in prokaryotes. Since bacteria without the complex are unable to survive, the complex is an attractive target for antimicrobials.

The comparative phylogeny of ribonuclease P makes it a good target for anti-infective development. The bacterial RNA and protein subunits differ from those of eukarya in sequence and in number. Eukaryal RNA components are not catalytic in vitro, and a chloroplast ribonuclease P may not have an RNA component at all. Eukaryal ribonuclease P enzymes also contain numerous protein components in contrast to the single bacterial one. These difference between bacterial and eukaryal ribonuclease P make it likely that inhibitors of bacterial ribonuclease P that have a high therapeutic index can be found or synthesized.

It is also contemplated that the targeting of ribonuclease P will lead to a pathogen-inhibiting agent with broad spectrum of action. Despite having very little primary sequence conservation, bacterial ribonuclease P species are much more similar to each other than to eukaryal species. While not wishing to be bound by theory, it is believed bacterial ribonuclease P RNAs fold into very similar secondary structures with a conserved core. A mutant strain of E. coli whose chromosomal gene for ribonuclease P RNA has been deleted can grow when transformed with a plasmid expressing the RNAs from any of several diverse bacterial species, both Gram-positive and Gram-negative. This points out the similarity of ribonuclease P RNAs. It is contemplated that these similarities make it likely that molecules targeting ribonuclease P will have a broad spectrum of action.

The protein and RNA components of ribonuclease P are not closely linked genetically. In one embodiment of the present invention, E. coli ribonuclease P RNA, the product of the rnpB gene, is synthesized from a strong promoter under stringent control. The transcript mostly terminates at a strong rho-independent site located immediately downstream of the mature RNA, read-through of this terminator allows the expression of a complex open reading frame whose function is unknown. The protein component, the product of the rnpA cistron, is synthesized from a large operon along with DnaA and ribosomal protein L34. The protein component (termed C5 in E. coli, and P protein in other genera) has apparently been selected for poor expression: the codon usage is unfavorable for high expression, the transcript contains little or no Shine-Dalgarno ribosome-binding sequence, and the initiator methionine codon is CUG instead of the AUG. In contrast, the RNA component is strongly expressed. It is contemplated that more RNA is normally transcribed than is necessary for enzyme biosynthesis with the excess being degraded.

The A49 mutant strain of E. coli (See, Schedl, P., and Primakoff, P. Proceedings of the National Academy of Sciences of the U.S.A. 70(7):2091-5, 1973) is temperature-sensitive for the synthesis of tRNA and has lowered levels of ribonuclease P activity than does its wild-type precursor. The mutation is a missense, Arg to His, at position 38 in the sequence of the protein subunit of ribonuclease P. The physiological effect of the mutation is somewhat paradoxical.

Although reduced in amount relative to that found in the wild-type strain, purified ribonuclease P holoenzyme from the mutant strain is not itself temperature-sensitive and is kinetically similar to wild-type ribonuclease P.

Rather than affecting activity, the rnpA 49 mutation affects assembly of the enzyme at high temperature. The rnpA 49 protein subunit has a lower affinity for its cognate RNA than does the wild type protein. Under nonpermissive conditions, the enzyme fails to assemble. Any pre-existing activity is diluted out over a few generations, leading to the cessation of cell growth.

When plasmid libraries of E. coli or other bacterial DNA are transformed into the A49 mutant strain, the cells that grow at 42° C. are transformed with one of two sequences. The first is rnpA (the homologue of the mutation, encoding the protein subunit) and the second is rnpB, the gene for the RNA component of the enzyme. Either sequence restores tRNA biosynthesis to a level compatible with growth, although the former is more effective. Relief of temperature-sensitivity by cloned rnpA sequences is easily rationalized since the sequences are homologous, but the basis for the ability of cloned sequences for the RNA component is less clear. Physiological and biochemical data indicate that the large excess of ribonuclease P RNA synthesized from the strong, high-copy promoter drives assembly of the holoenzyme by mass action. The overall phenomenon of relief of a mutation by overproduction of an interacting component is one form of multicopy suppression. Multicopy suppression of rnpA 49 by clones containing rnpB gene is more sensitive than its ability to confer growth on a strain deleted for the rnpB sequence. For example, all the transition mutants in rnpB that were isolated on the basis of their ability to suppress the rnpA 49 mutation were fully able to support growth of the strain whose chromosomal copy of ribonuclease P RNA was deleted. It is contemplated that the weak binding of the mutant A49 protein sensitizes the system so that the native RNA structure is required for growth under nonpermissive conditions.

Illustratively, the expected growth patterns caused by an inhibitor of ribonuclease P assembly for the different strains are provided in FIG. 1. Note that the primary screening system (lower left in FIG. 1) ensures that the compound is bioactive while the secondary screen ensures that the compound targets ribonuclease P. This is a useful distinction because:

(1) Compounds that have targets other than ribonuclease P, whether or not they have additional effects on ribonuclease, will inhibit the growth of both strains. For example, puromycin inhibits the growth of both strains because it has a ribosomal target (which is more susceptible than is ribonuclease P to the drug). Similarly, neomycin B would inhibit the growth of both strains because it acts on the ribosome. Compounds that fit the screening target are therefore contemplated to affect ribonuclease P primarily.

(2) The strain is resistant to the beta-lactams by virtue of the vector plasmid. Additional resistance markers may be engineered into the indicator strains to eliminate other antibiotics of known mechanism. Thus, for example, introduction of an aminoglycoside resistance marker derived from the transposon Tn5 by cloning into the vector plasmid would render the resulting strain resistant to aminoglycosides.

(3) Compounds that are identified in the screen are determined to be inhibitory to growth at an early stage of screening, rather than merely being inhibitors of a biochemical reaction.

(4) General poisons are identical and eliminated from the set of lead compounds at the second stage of screening since they will inhibit the growth of the strain carrying multicopy ribonuclease P RNA genes. This feature increases the chances that compounds with a useful therapeutic index will be identified.

The agents targeting ribonuclease P system described above are an example of a Class 2 system. Since the rnpA 49 mutation is suppressed by the homologous functionality, agents targeting ribonuclease P directly or its assembly would also be identified by the screening protocol.

In practicing the present invention, a pathogen, for example, a bacterial, fungal or viral strain, is contacted with test sample. This mixture is maintained under appropriate conditions and for a sufficient time to allow interaction of the test sample with the pathogen. Experimental conditions are determined empirically for each pathogenic strain tested. The time necessary for interaction of test sample with pathogen will vary depending on the test sample, the pathogenic strain (for example, replication time of the pathogen), and other conditions used. Other experimental conditions that are optimized for each pathogen strain include pH, reaction temperature, salt concentration and composition, divalent cation concentration and composition, reducing agent concentration and composition, and the inclusion of non-specific protein and/or nucleic acid in the assay. When screening chemical or natural product libraries a consideration is the response of the assay to organic solvents (for example, dimethyl sulfoxide (DMSO), methanol or ethanol) commonly used to re-suspend such materials. Accordingly, in one embodiment of the present invention, each pathogenic strain utilized in the screening is tested for cytotoxicity in the presence of varying concentrations of each of these organic solvents. Another consideration is that the assay may also be particularly sensitive to certain types of compounds, for example, intercalating agents, that commonly appear in chemical and especially natural product libraries. These compounds can often have potent, but non-specific, inhibitory activity. Some of the buffer components and their concentrations can be specifically chosen in anticipation of this problem. For example, bovine serum albumin will react with radicals and minimize surface adsorption. The addition of non-specific DNA or RNA may also be necessary to minimize the effect of nucleic acid-reactive molecules (such as, for example, intercalating agents) that would otherwise score as "hits" (a false positive) in the assay.

EXAMPLES

The present invention is further illustrated by the following examples, which should not be construed as limiting in any way. The practice of the present invention will employ, unless otherwise indicated, conventional techniques of microbiology, pharmacology and pharmaceutics, which are within the skill of the art.

Example 1

Strains. E. coli DH5alpha strains and the clinically isolated bacterial cells used are described in Table No. 2.

TABLE NO 2

*E. coli* strains (DH5alpha) and other bacterial cells utilized

| Strain | Host | Relevant phenotype | Genotype | Source or Reference |
|---|---|---|---|---|
| DM 46 | E. coli DH5 alpha | Wild type | rnpB (chromosomal) rnpB (high copy plasmid) amp$^r$ (vector) | D. Morse, Ph.D. dissertation University of MO-Columbia 1991 |
| DM 100 | E. coli DH5alpha | Control | rnpB + (chromosomal amp$^r$ (19R/PTZ) | D. Morse, Ph.D. dissertation University of MO-Columbia 1991 |
| *Pseudomonas aeruginosa* | | clinical isolated pathogen | | Shraddha Subtankar University of MO-Columbia 1996 |
| Streptococcus | | clinical isolated pathogen | | Shraddha Subtankar University of MO-Columbia 1996 |
| *Klebsiella pneumoniae* | | clinical isolated pathogen | | Shraddha Subtankar University of MO-Columbia 1996 |
| Salmonella spp. | | clinical isolated pathogen | | Shraddha Subtankar University of MO-Columbia 1996 |
| *Staphyloccocus aureus* | | clinical isolated pathogen | | Shraddha Subtankar University of MO-Columbia 1996 |

Chemicals and Media. $^{32}P_i$ ($H_3PO_4$) was obtained from NEN Research Products. Ampicillin (Ap), was purchased from the University of Missouri Hospital, and was used at 50 g/ml. Diethyl pyrocarbonate (DEPC) and dimethyl sulfoxide (DMSO) were purchased from Sigma Chemical Company. A library of 700 plant extracts that was used is described in Table No. 3.

TABLE NO 3

Type of extract used in this work

| Type of extract | Number of extract tested | Collection II Professor S. M. Hecht University of Virginia |
|---|---|---|
| Hexane | 172 | (B819194-2)-(B855431-2) |
| Methanol | 400 | (B819194-4)-(B855431-4) and |
| Methyl Ethyl Ketone | 130 | (B855577-4)-(B855913-4) (B855205-7)-(B855431-7) |

PEN Assay broth contained (per 250 ml) 0.375 g bacto beef, 0.375 g yeast extract, 1.25 g peptone, 0.25 g dextrose, 0.92 g dipotassium phosphate, 0.33 g monopotassium phosphate, and 0.85 g sodium chloride (Difco Laboratories). TSA broth contained (per 100 ml) 1.5 g bacto tryptone, 0.5 g bacto soytone, and 0.5 g sodium chloride (Difco Laboratories).

TSA media (plate) was made by adding 1.5 g bacto agar to the above media. Low phosphate media was prepared (per liter) from 5 ml of 200 µl concentrated of trace salt, 6.05 g tris base, 1.5 g KCl and 1.0 g ($NH_4$)$_2$$SO_4$ pH adjusted to 7.4. For labeling with $^{32}P$, TB media was supplemented with 0.2% glucose and 0.6% peptone. MacConkey agar base plate was prepared from (per liter) 40 g MacCokney agar and 2.5 g lactose.

Methods. Different strains of *E. coli*-DH5alpha (DM46 and PTZ/19R) were streaked onto bacto MacConkey agar base plate containing ampicillin at 50 µg/ml. Then a fresh single colony was grown on 5 ml NZY Ap (50 µg/ml) broth at 37° C. overnight. The next day a frozen cell from the above cells was made. 1 ml of a freshly saturated culture was added to a microcentrifuge tube containing 1 ml DMSO (7%). These cells were stored at −80° C. Cells from frozen stocks were streaked out again and one colony from each plate was transferred to 1 ml NZY(amp, 50 µg/ml) broth. The tubes were shaken at 37° C. overnight.

Top agar (1% tryptone, 0.8% NaCl, 0.7% agar) was used to distribute cells in a thin layer over the surface of a plate. 100 µl of fresh cell was mixed with 2.5 ml top agar. The mixture was then poured into NZY AP (50 µg/ml). Microtiter dishes containing 96-well, were used to prepare serial dilutions in 10% DMSO (1:5, 1:25, 1:125, 1:625) of extracts. A multichannel pipeting device was used to add 5 µl extract to the top agar plate. Agar plates containing extract were incubated overnight at 37° C. At the end of incubation, inhibition appeared as clear zone around the place that extract was added. Positive extracts from the initial screens were analyzed further.

a. Disk Assay Method. Sterile forceps were used to remove a single disk from the vial of bacto sterile disks. Sterile disks containing 5 µl of positive extract were placed (at least 20 mm apart) on the surface of the top agar plates.

Disks were gently touched with the tip of forceps to insure proper contact. Top agar plates were inverted and incubated at 37° C. overnight. Then these plates were examined for zones of inhibition of the tester cell.

b. Plate Efficiency of Positive Extract. In this assay two groups were used: experiment group and control group.

For experiment group, overnight cultures of tester cells (19R, DM46) were diluted, $10^0$, $10^2$, $10^4$, $10^5$, $10^6$, $10^7$ into PEN Assay broth containing 50 µg/ml amp. 100 µl of these cells were mixed with 1 ml top agar and 40 µl diluted positive extract (1:10, 1:100, 1:1000). The resulting mixture was poured onto a PEN Assay agar base plate (Difco Laboratories) and incubated overnight at 37° C.

For control group, the assay was the same except 10% DMSO was used instead of positive extracts. The next day, the number of colonies in each plate was counted.

c. Minimum Inhibitory Concentration (MIC) assay. Minimum Inhibitory Concentration Assay was performed on plate, as well as in broth. The lowest concentration of positive extracts that prevent the growth of 19R/PTZ, but not DM46 strain were reported as the Minimum Inhibitory Concentration. Various concentration of active extracts (1:10, 1:20, 1:40 dilution) were made in 10% DMSO. These extracts then were added to a series of test tubes containing 1 ml PEN Assay broth (50 µg/ml AmP) which were inoculated with $10^7$ and $10^5$ dilution of freshly prepared overnight culture of the 19R/PTZ and DM46 strain. These cells were grown at 37° C. overnight. The highest dilution of active extracts which completely inhibited the growth of an organism was used as the Minimum Inhibitory Concentration.

The Minimum Inhibitory Concentration was also determined using PEN Assay agar plate. The same assay was utilized with one slight change. The PEN Assay agar was used instead of PEN Assay broth.

d. Mode of Action. 5 µl of culture (from above) that did not grow was removed and added to 1 ml of fresh broth (PEN Assay broth containing 50 µg/ml) which then were grown at 37° C. Those extracts where the cell grew within 24 hours after dilution were reported as bacteriostatic.

Clinical Application of Positive Extracts. The same assays as were discussed in part a, b and c were utilized to test the inhibitory affects of positive extracts on the growth of clinical isolates of gram-negative and positive pathogens. The results of these experiments will be explained in detail in below.

Cell Growth Conditions. Overnight cultures of strains DM46 and PTZ/19R were made by transferring cells from a single colony of each strain to a tube containing 1 ml low phosphate medium and shaking at 37° C. overnight. 5 ml pre-warmed medium (low phosphate medium) was reinoculated with 100 µl fresh overnight culture, which was grown in the same manner. These cells were allowed to grow to an optical density of 0.2 at 600 nm (about 2 hours). At this point positive extracts (20 µg/ml, MIC) were added to the above growing cells. These cells were permitted to grow to mid-log by measuring the $OD_{600}$ of growing culture at different times in growing cycle. A photoelectric colorimeter (Klett) was used to determine the optical density. In this case, cells were grown to Klett 30. At this time extract was added and Klett was measured at different times in growing cycle.

Cell Labeling with $^{32}P$. The freshly overnight culture was diluted 1:50 with low phosphate T media (containing 50 µg/ml Ap) and allowed to grow to an optical density of 0.2 (about 2 h). Then positive extract (20 µg/ml, MIC) was added to the above growing cells. When these reached an $OD_{600}$ of 0.4, they were labeled with inorganic $^{32}P$ (50 µCi/ml) for 20 minutes in water bath.

Sample Processing. After labeling, samples were processed by pipeting 300 µl of culture into 1 ml ice cold 80% ethanol, 1% diethyl pyrocarbonate stop solution. The mixture was kept in ice for 10 minutes and then centrifuged. After centrifugation for 10 minutes at 2000 rpm, the supernatants were discarded and tubes were drained onto tissues.

The pellet of cells was suspended in 80 ml of lysis buffer (1% SIDS, 10 mM tris, 10 mM $Na_2EDTA$, 40% glycerol, 0.1% bromophenol blue, 1% DEP, pH was adjusted with HCl to 7.4) and heated at 100° C. for 2 minutes to complete lysis. Samples were applied to a gel the next day.

Measurement of total $^{32}P$ incorporation. Before samples were applied to the gel, the amount of $^{32}P$ incorporated to RNA was measured. A sample of 1 ul from the culture being analyzed was added to a filter paper (Whatman) then transferred into a scintillation vial containing 5 ml Scintiverse E scintillation cocktail. The amounts of radioactivity incorporated into RNA molecules were determined using liquid scintillation analyzer, Packard Instrument Company, in order to compare the radioactivity incorporated into tRNA, rRNA, 5S, 4.5S,10S RNA for the experimental group with the control group.

Polyacrylamide Gel Electrophoresis of RNA. Cell lysates were subjected to electrophoresis on polyacrylamide gel slabs. All gel solutions, except ammonium per sulfate (APS) and $N,N,N^1,N^1$-tetra-methylethylenediamine (TEMED) were mixed in a suction flask and degassed for 15 minutes. The remaining components were added and mixed by gentle swirling. The solution then was poured between the glass plates which were siliconized with Sigmacote™ (Sigma Chemical Company).

A discontinuous (5%/12%) polyacrylamide gel was used to analyze small RNAs. The (12%) resolving gel (lower layer) contains (7.2 g/ml) 24 ml acrylamide (acrylamide:bisacrylamide 30:0.8), 12 ml TBE buffer, 400 µl APS and 24 µl TEMED. The lower layer then overlaid with water-saturated butanol. Polymerization was completed in about 45 minutes. Then the overlay solution was removed by inverting the slab gel.

The top of the gel was rinsed with water. The upper layer (stacking gel) was the same as the lower layer, with the exception that 10 ml acrylamide (5%) was used in place of 24 ml acrylamide.

The same amount of radio-activity cpm/min (249000 cpm/min or $8.3 \times 10^{-3}$ µCi) were loaded in each well. Electrophoresis was carried out for 3 hours at 160V or until the bromophenole blue dye marker reached about 1 cm from the bottom of the gel. The anode and cathode chambers contained the same butter (1×TBE). The gel were dried and autoradiographed.

Quantitation of Gel. Quantitation was accomplished by cutting the appropriate RNA bands from the dried gel. The positions of rRNA, tRNA, 4.5S RNA, 5S RNA and 10S bands in polyacrylamide gels were identified by autoradiography.

Slices were excised with a razor blade, added to a vial containing 5 ml Scintillation cocktail. The radioactivity incorporated into RNA was determined using a Scintillation counter.

Results. The assays described above were utilized to identify active crude extracts from a library of 700 plant extracts (Table No. 3).

Extract 8855575-4 inhibited the growth of our engineered E. coli cell (19R/PTZ) strain containing a single chromosomal copy of the wildtype rnpB gene while not affecting the growth of strain DM46, which contains the rnpB gene cloned on a high copy plasmid.

Serial dilution of extracts were made in 10% DMSO and these dilutions were tested for their ability to inhibit the growth of the tester strain (Table No. 4).

Five of the 14 initial positive extracts reproducibly inhibited the growth of 19R/PTZ strain completely. The remainder were partially active against DM46 and were not studied at this time, as they were not considered to be likely inhibitors of RNaseP assembly.

TABLE NO 4

List of 14 Initial Active Crude Extracts and Their Inhibitory Effect

| | | 1:5 dilution (Ex) | | 1:2 dilution (Ex) | |
|---|---|---|---|---|---|
| # | Full Name | Strain Inhibitor | No Strain Inhibitor | Strain Inhibitor | No Strain Inhibitor |
| 1 | B855548-4 | 19R/PTZ* | DM46 | 19R/PTZ* DM46** | |
| 2 | B855514-4 | 19R/PTZ* | DM46 | 19R/PTZ* DM46** | |
| 3 | B855575-4 | 19R/PTZ* | DM46 | 19R/PTZ* | DM46 |
| 4 | B855833-4 | 19R/PTZ* | DM46 | 19R/PTZ DM46** | |
| 5 | B855205-4 | 19R/PTZ* | DM46 | 19R/PTZ* DM46** | |
| 6 | B855318-4 | 19R/PTZ* DM46** | | 19R/PTZ* DM46** | |
| 7 | B855345-4 | 19R/PTZ* DM46** | | 19R/PTZ* DM46** | |
| 8 | B855323-4 | 19R/PTZ* DM46** | | 19R/PTZ* DM46** | |
| 9 | B855410-4 | 19R/PTZ* DM46** | | 19R/PTZ* DM46** | |
| 10 | B855230-4 | 19R/PTZ* DM46** | | 19R/PTZ* DM46** | |
| 11 | B855206-4 | 19R/PTZ* DM46** | | 19R/PTZ* DM46** | |
| 12 | B855405-2 | 19R/PTZ* DM46** | | 19R/PTZ* DM46** | |
| 13 | B855414-2 | 19R/PTZ* DM46** | | 19R/PTZ* DM46** | |
| 14 | B854925-5 | 19R/PTZ* DM46** | | 19R/PTZ* DM46** | |

*strong
**weak

Initial screenings of the extracts revealed that methyl ethyl ketone extracts were general inhibitors. All extracts from this class inhibited the growth of both 19R/PTZ and DM46 strains Therefore, these extracts were eliminated from further investigation.

Disk Assay Method. The result of this experiment indicated that the extracts were not diffusible from the assay disks. The solubility of these extracts in organic solvents potentially made them poorly soluble in water. As a result, no clear zone was observed around the place that the extract was added.

Efficiency of Plating (E.O.P.) Assay. The efficiency of plating and the lowest concentration of positive extracts that inhibited the growth of our engineered $E. coli$ cells were determined. Serial dilutions ($10^0$, $10^2$, $10^4$, $10^5$, $10^6$, $10^7$) of overnight saturated fresh cells in PEN Assay broth (containing 50 μg/ml amp) were made. PEN Assay plates were prepared the same day that the sample was tested. After the PEN Assay Agar was solidified, it was overlaid with 400 μl of diluted extract (1:10, 1:100) which were previously mixed with 100 μl of diluted organism and 1 ml top agar. These plates were incubated at 37° C. overnight.

After overnight incubation, a lawn of bacteria was observed on plate containing the following dilutions of the test organism, $10^0$, $10^1$, $10^2$, $10^3$, $10^4$. The inhibition was found to be quite gradual in a series of organism dilution. In many instances higher dilutions of organism ($10^5$, $10^7$) were required to show inhibition. The control dilutions were treated identically except that 10% DMSO was used in place of the extract.

The plate efficiency of positive extract B855833-4 is summarized in Table No. 5. The plate efficiency of extract B855575-4 is shown in Table No. 6.

TABLE NO 5

Plate Efficiency of Positive Extract B855833-4

| Dilution (organism) | 19R + Extract (# of colony) | | 19R + DMSO 10% | DM46 + Extract (# of colony) | | DM46 + DMS O10% |
|---|---|---|---|---|---|---|
| | 1:10 | 1:100 | | 1:10 | 1:100 | |
| $10^5$ | 400 | 800 | 1000 | 1000 | Lawn of bacteria | Lawn of bacteria |

TABLE NO 6

Plate Efficiency of Positive Extract 8855575-4

| Dilution organism | 19R + Extract (# of colony) | | 19R + DMS O10% | DM46 + Extract (# of colony) | | DM46 + DMS O10% |
|---|---|---|---|---|---|---|
| | 1:10 | 1:100 | | 1:10 | 1:100 | |
| $10^5$ | 10 | 80 | 900 | Lawn of bacteria | Lawn of bacteria | Lawn of bacteria |

These data indicated that this extract (8855575-4) is a very strong inhibitor of the $E. coli$ engineered cell (19R/PTZ) while not affecting the growth strain DM46. Since the B855575-4 extract was inhibitory to $E. coli$ (19R/PTZ) but non-inhibitory to $E. coli$, overexpressing the RNA component of RNaseP (DM46), it was concluded that this extract could be a good candidate for inhibitors of RNaseP assembly.

Minimum Inhibitory Concentration (MICI). The lowest concentration of extract that prevented growth was reported as the minimum inhibitory concentration.

Calculation for MIC results. The original concentration of extract was about 5 mg/ml.

The volume of extract that was used in this assay was about 0.04 ml. Therefore, the amount of extract could be calculated as follows: 5 mg/ml×0.04 ml=0.2 mg or 200 μg.

A 0.2 mg extract was diluted in 1 ml top agar. Therefore, the amount of extract in 1 ml agar was equal to 200 μg/ml. It was assumed that only 1% of these crude extracts were the active principle; therefore the amount of active compound was approximately 2 μg/ml.

The molecular weight (mw) of these extracts was estimated to be about 0.4 mg/mmol or 400 μg/umol (Professor S. M. Hecht, personal communication). Moreover, the final concentration of extract that inhibited the growth of 19R/PTZ was obtained using the following formula.

$$\frac{2\ \mu g/ml}{400\ \mu g/umol} = 0.005\ \mu mol/ml\ or\ 5\ \mu M$$

Clinical Isolated Bacterial Cell. Identical assays (plate efficiency, MIC, disc assay) were utilized to test the effectiveness of positive crude extracts in terms of clinical application, except TSA plates were used instead of PEN Assay media.

$10^5$ dilution of overnight saturated fresh cells (*P. aeruginosa, Staphylococcus aureus*, Strep) in PEN Assay broth (containing 50 μg/ml Amp) were made. 100 μl of diluted cell then was mixed with 1 ml top agar and 400 μl of diluted extract (1:10). The resulting mixture was poured onto a PEN Assay Agar plate. These plates were incubated at 37° C. overnight.

The following extracts were tested.
1. B855410-4
2. B855230-4
3. B855575-4

TABLE NO 7

Inhibitory Effect of B855575-4 on the Growth of Clinical Isolate Bacterial Cell

| Bacterial cell | 1:10 (Ex) # of Colony | Control (only 10% DMSO) |
|---|---|---|
| *P. aeruginosa* | 65 | 400 |

TABLE NO 8

Inhibitory Effect of B855410-4 on the growth of Clinical Isolate Bacterial Cell

| Bacterial cell | 1:10 (Ex) | Control (only 10% DMSO) # of Colony |
|---|---|---|
| *P. aeruginosa* | 300 | 400 |
| Streptococcus | 60 | 400 |

TABLE NO 9

Inhibitory Effect of B855230-4 on the growth of Clinical Isolate Bacterial Cell

| Bacterial cell | 1:10 (Ex) | Control |
|---|---|---|
| *P. aeruginosa* | 350 | 400 |
| Streptococcus | 120 | 400 |

Strong inhibition was observed when extracts #1 and #2 were added to *Streptococcus* containing media. However, these extracts were not able to inhibit the growth of *Staphylococcus*, which is a strong pathogen.

The above extracts were then also added to the gram negative bacterial cell, *Pseudomonas aeruginosa*. The first two extracts did not have any effect on these cells. However, extract B 855575-4 showed inhibitory affects on these cells.

Mode of Action. It is known that antibacterial drugs exert their effects on bacterial cells in two ways: either by killing them (bacterialcital) or by inhibiting their growth (bactertiostatic).

In order to determine the mode of action of our positive extracts (either killing or inhibiting), serial dilution of these extracts (1:10, 1:20, 1:40) in 10% DMSO were made in 96 wells microtiter dishes. These extracts then were added to a series of test tubes containing 1 ml PEN Assay broth (50 μg/ml) which were inoculated with $10^7$ dilution of freshly prepared overnight culture of the 19R/PTZ and DM46 strain as well as clinical isolated bacterial cell. These cells were grown at 37° C. overnight. The activity of extract (B 855575-4) against these strains was tested three times and the following results were obtained in each experiment (Table No. 10).

TABLE NO 10

The Mode of Action of Positive Extract B855575-4

| Bacterial cell | 1:10 (Ex) | 1:20 (Ex) | 1:40 (Ex) | Control (no extract, only DMSO) |
|---|---|---|---|---|
| 19 R | No G | No G | G | G |
| DM46 | G | G | G | G |
| Staph | G | G | G | G |
| *Pseudomonas* | No G | No G | G | G |

After overnight incubation, the 5 μl of culture that did not grow was removed and added to 1 ml of fresh broth, which was then grown at 37° C. overnight.

These cells were kept under observation for one week. The results are shown in Table No. 11.

TABLE NO 11

| Bacterial cell | 1:10 | 1:20 | Control (No Ex) |
|---|---|---|---|
| 19R | No G (for 6 days) | No G (for 6 days) | G |
| Pseudomonas | No G (for 4 days) | No G (for 4 days) | G |

Since the extract B855575-4 inhibited the growth of 19R/PTZ strain and *P. aeruginosa* after overnight incubation, it was concluded that this extract could be bacterialcital. However these cells start growing after six days. The following factors might have caused the cell growth after six days, contamination of the broth or growth of other cells in media other than *E. coli*. It is important to note that (B855575-4) extract was inhibitory to the growth of gram negative bacteria (*E. coli* and *Pseudomonas*). A similar experiment was conducted for positive extracts B855548-4 and B855205-4. The results are shown in Table Nos. 12 and 13 respectively.

TABLE NO 12

The Inhibitory Effect of B855548-4

| Bacteria | 1:10 (Ex) | 1:20 (Ex) | 1:40 (Ex) | Control (No Ex) |
|---|---|---|---|---|
| 19R | No G | G | G | G |
| DM46 | G | G | G | G |
| Staph | No G | G | G | G |
| *Pseudomonase* | No G | G | G | G |

5 μl of culture that did not grow was removed and added to 1 ml fresh broth. These cells were grown at 37° C. overnight. Results are illustrated in Table No. 13.

TABLE NO 13

| Bacteria | 1:10 | 1:20 |
|---|---|---|
| 19R/PTZ | G (overnight) | G |
| Staph | G (overnight) | G |
| *Pseudomonase* | G | G |

TABLE NO 14

The Inhibitory Effect of B855205-4

| Bacteria | 1:10 (Ex) | 1:20 (Ex) | 1:40 (Ex) | Control (No Ex) |
|---|---|---|---|---|
| 19R/PTZ | No G | G | G | G |
| DM46 | G | G | G | G |
| Staph | No G | G | G | G |
| *Pseudomonase* | No G | No G | G | G |

5 μl of culture that did not grow was removed and added to 1 ml fresh broth. These cells were grown at 37° C. overnight. Results are shown in Table No. 15.

TABLE NO 15

| Bacteria | 1:10 | 1:20 |
|---|---|---|
| 19R/PTZ | G (overnight) | G |
| Staph | G (overnight) | G |
| *Psedumonase* | G | G |

These two positive extracts inhibited the growth of bacterial cell 19R/PTZ strain, *Pseudomonas* and *Staphylococcus* on the first day. Then on the second day and after, they started growing gradually. It was concluded that these extracts were not bacterialcital.

In conclusion, plant extracts (potential antimicrobials) were identified which were non-inhibitory to an *E. coli* engineered strain bearing an rnpB (encoding RNA subunit of RNaseP) gene cloned on a high copy vector (DM46), but inhibitory to an *E. coli* strain contains the vector plasmid, but only chromosomal copy of rnpB gene (19R/PTZ). These plant extracts were inhibitory to the growth of gram-negative, gram-positive or both pathogens.

The Effect of Positive Extracts on RNaseP. In the second phase of the study these extracts were investigated for their inhibition of RNaseP assembly or if they possibly interfered with other factors that were essential for cell growth.

A previous study (Baer, et al., 1989; Schedl, et al. 1975) showed that tRNA precursors accumulate when cells bearing rnpA 49 (a mutation in the C5 protein, the protein moiety of the RNaseP homoenzyme) were shifted from permissive temperature to non-permissive temperature. Moreover, Apirion and Watson (1979) found that mutant rnpB (gene coding for M1 RNA) affects the function of RNaseP. Hence, tRNA precursors are accumulated under these conditions.

Non-functional RNaseP also can be identified by either the appearance of a 19SRNA molecule, which contains 16S rRNA and spacer tRNA, and of a number of tRNA precursor molecules, or by the disappearance of the 4.5S RNA molecule (Gegenheimer and Apirion, 1978).

Cell Growth Conditions. Growth measurements were made with a photoelectric calorimeter (Klett). *E. coli* strains 19R/PTZ and DM46 were grown to a Klett value of 30. At this time, extract was added and culture density was measured at different times in the growing phase.

Figure 4:
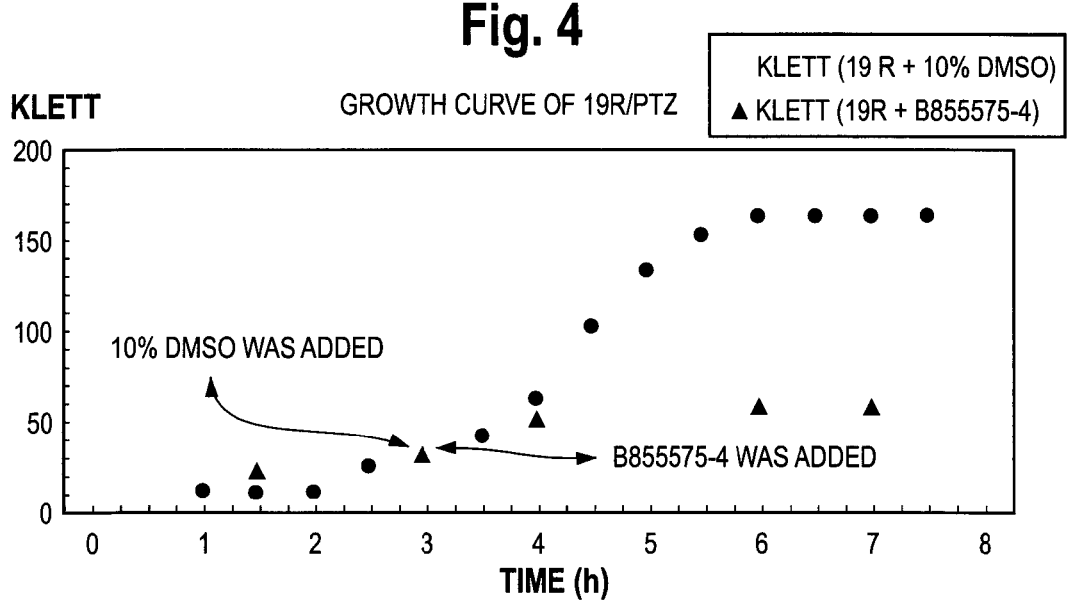
FIG. 4 illustrates the growth curve of 19R/PTZ in the presence of 20 μg/ml extract B855575-4 (triangles) and 10% DMSO (diamonds) added at time 3 hours.
Figure 5:
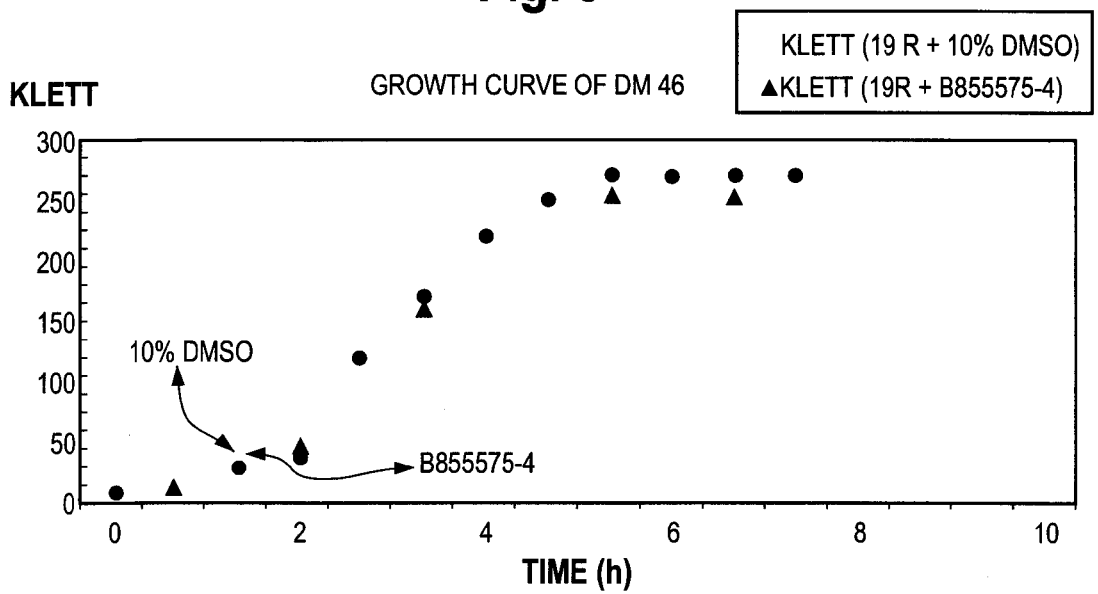
FIG. 5 illustrates the growth curve of DM 46 in the presence of 20 μg/ml extract B855575-4 (triangles) and 10% DMSO (diamonds) added at time 90 minutes.

FIGS. 4 and 5 respectively illustrate both the effect of positive extract (B855575-4) on the growth rate of 19R/PTZ as well as on DM46 strain.

FIG. 4 demonstrates that extract B855575-4 inhibited growth of *E. coli* in broth containing 19R/PTZ after a short time. Our results indicated that these cells grew for only 90 minutes after addition of extract. However, for control group (19R/PTZ+10% DMSO) cells reached the stationary phase after 7 hours (Klett 150).

In contrast, the growth of strain DM46 was not inhibited when 20 μg/ml of extract (B855575-4) was added. Likewise, the similar growth rate was obtained when 10% DMSO was added to DM46 strain (FIG. 5).

These results confirm the previous findings that the B855575-4 extract inhibited the growth of an *E. coli* strain (19R/PTZ), but not *E. coli* (DM46) over expressing the RNA subunit of RNaseP.

Cell Labeling with $^{32}$P. In this experiment, the following positive extracts were added at a concentration of 20 μg/ml to 19R/PTZ and DM46 strains at Klett 30.

1. B855575-4
2. B855205-4
3. B855833-4
4. B855230-4
5. B855414-2

These cells then were allowed to grow to Klett 50 (1 h). After 1 hour of growth, they were labeled with $^{32}$P (50 μCi/ml) for 20 minutes. After labeling, the samples were processed and the total $^{32}$P that were incorporated into RNA molecules were measured using scintillation counter. The results are shown in Table No. 16.

TABLE NO 16

The Amount of Radioactivity Incorporated to RNA

| Sample | cpm (1 μl of sample) | Amount of RNA used for clectrophoresis gel (cpm) |
|---|---|---|
| 19R + 10% DMSO (control) | 72100 | 249000 |
| 19R + B855575-4 | 14505 | 249000 |
| 19R + B855205-4 | 118372 | 249000 |
| 19R + B855833-4 | 122919 | 249000 |
| 19R + B855230-4 | 175075 | 249000 |
| 19R + B855414-2 | 109720 | 249000 |
| DM46 + 10% DMSO (control) | 66592 | 249000 |
| DM46 + B855575-4 | 133172 | 249000 |
| DM46 + B855205-4 | 71116 | 249000 |
| DM46 + B855833-4 | 15695 | 249000 |
| DM46 + B855230-4 | 49068 | 249000 |
| DM46 + B855414-2 | 102531 | 249000 |

Cell lysates were subjected to electrophoresis on a discontinuous polyacrylamide gel (5%/12%). The same amount of radioactivity cpm/min (249000 cpm/min or $8.3 \times 10^{-3}$ μCi) were loaded in each well. Electrophoresis was carried out for 3 hours until the bromophenol blue dye marker reached about 1 cm from the bottom of the gel.

Quantitation of Gel. The position of rRNA, 5S RNA, 4.5S RNA and 10S (for both 19R/PTZ and DM46) in 5%/12% polyacrylamide gel were identified by autoradiography. These bands were excised from the gel and the radioactivity incorporated in RNA was determined using scintillation counter. The ratio of tRNA/rRNA, tRNA/5S, tRNA/4.5S, tRNA/10S for both experimental and control group were calculated for six positive extracts as shown in Table No. 17.

TABLE NO 17

The Ratio of tRNA/rRNA, tRNA/5S, tRNA/4.5S, tRNA/10S

| Strain | tRNA/rRNA | tRNA/5S | tRNA/4.5S | tRNA/10S |
|---|---|---|---|---|
| 19R + DMSO | 0.11 | 2.5 | 6.2 | |
| 19R + B855575-4 | 0.5 | 6 | 13 | 7 |
| 19R + B855205-4 | 0.3 | 10 | 7.5 | 9 |
| 19R + B855833-4 | 0.47 | 6.67 | 16 | 9.1 |
| 19R + B855230-4 | 1.6 | 8 | 10 | 6.8 |
| 19R + B855414-2 | 0.36 | 6.4 | 4.45 | 12 |
| DM46 + DMSO | 0.14 | 1 | 2 | |
| DM46 + B855575-4 | 0.16 | 1.8 | 2.2 | |
| DM46 + B855205-4 | 0.17 | 4.2 | 2.8 | |
| DM46 + B855833-4 | 0.15 | 1.5 | 2.2 | |
| 19R + B855230-4 | 0.14 | 1 | 1 | |
| 19R + B855414-2 | 0.1 | 2.4 | 2 | |

Previous work (Heng Jing dong, et al., 1996) showed that there is a 50% reduction in the mass ratio of total tRNA/rRNA as growth rates are increased from 0.4 to 2.5 doublings per hour. The data above showed that in the presence of positive extracts (as shown in FIG. 6) the ratio of tRNA/rRNA increased by 5-10 fold in comparison to the control group (19R+10% DMSO). The present results indicated that the ratio of tRNA/rRNA were the same for DM46 strain in the absence or presence of the positive extracts as shown in Table No. 19.

Statistical Analysis of Our Study. The ratio of tRNA/rRNA, tRNA/5S, tRNA/4.5S RNA and tRNA/10S were obtained for both control group (19R+DMSO and DM46+DMSO) experiment group (19R/PTZ+Extract and DM46+Extract). Student's T test was conducted, and the statistical findings were based upon assumption that the control group (19R+10%. DMSO) is considered as the independent variable whereas, the experimental group (19R+extract) is dependent variable. The summary of the result of each positive extract are shown in the following tables.

TABLE NO 18

The Result of Student T Test for Extract B855575-4

| source | T test | T value 0.05 | 0.01 | df* | Result 0.05 | 0.01 |
|---|---|---|---|---|---|---|
| tRNA/rRNA | 3.5 | 2.77 | 4.60 | 4 | sig. | not sig. |
| tRNA/5S | 1.9 | 2.77 | 4.60 | 4 | not sig. | not sig. |
| tRNA/4.5S | 3.9 | 2.77 | 4.60 | 4 | sig. | not sig. |
| tRNA/10S | 4.12 | 2.77 | 4.60 | 4 | sig. | not sig. |

*df, degree of freedom
*If T test > T value, the difference between two means is statistically significant.
**If T test < T value, the difference between two means is not statistically significant.

TABLE NO 19

The Results of Student T Test for Extract B855205-4

| source | T test | T value 0.05 | 0.01 | df* | Result 0.05 | 0.01 |
|---|---|---|---|---|---|---|
| tRNA/rRNA | 4.89 | 2.44 | 3.70 | 6 | sig. | sig. |
| tRNA/5S | 5.48 | 2.77 | 4.69 | 4 | sig. | sig. |
| tRNA/4.5S | 0.3 | 2.77 | 4.69 | 4 | not sig. | not sig. |
| tRNA/10S | 2.9 | 2.77 | 4.69 | 4 | sig. | not sig. |

*df, degree of freedom
*If T test > T value, the difference between two means is statistically significant.
**If T test < T value, the difference between two means is not statistically significant.

TABLE NO 20

The Result of Student T Test for Extract B855833-4

| source | T test | T value 0.05 | 0.01 | df* | Result 0.05 | 0.01 |
|---|---|---|---|---|---|---|
| tRNA/rRNA | 9.12 | 2.44 | 3.70 | 6 | sig. | sig. |
| tRNA/5S | 0.6 | 2.44 | 3.70 | 6 | not sig. | sig. |
| tRNA/4.5S | 2.26 | 2.77 | 3.70 | 4 | not sig. | sig. |
| tRNA/10S | 1.36 | 2.77 | 3.70 | 4 | not sig. | sig. |

*df, degree of freedom
*If T test > T value, the difference between two means is statistically significant.
**If T test < T value, the difference between two means is not statistically significant.

TABLE NO 21

The Result of Student T Test for Extract B855230-4

| source | T test | T value 0.05 | 0.01 | df* | Result 0.05 | 0.01 |
|---|---|---|---|---|---|---|
| tRNA/rRNA | 2.5 | 2.44 | 3.70 | 6 | sig. | not sig. |
| tRNA/5S | 0.58 | 2.44 | 3.70 | 6 | not sig. | not sig. |
| tRNA/4.5S | 2.07 | 2.77 | 3.70 | 4 | not sig. | not sig. |
| tRNA/10S | 2.04 | 2.77 | 3.70 | 4 | not sig. | not sig. |

*df, degree of freedom
*If T test > T value, the difference between two means is statistically significant.
**If T test < T value, the difference between two means is not statistically significant.

TABLE NO 22

The Result of Student T Test for Extract B855414-2

| source | T test | T value 0.05 | 0.01 | df* | Result 0.05 | 0.01 |
|---|---|---|---|---|---|---|
| tRNA/rRNA | 2.47 | 2.44 | 3.70 | 6 | sig. | not sig. |
| tRNA/5S | 7 | 2.77 | 4.60 | 4 | sig. | sig. |
| tRNA/4.5S | 0.74 | 2.77 | 4.60 | 4 | not sig. | not sig. |
| tRNA/10S | 1.18 | 2.77 | 4.60 | 4 | not sig. | not sig. |

*df, degree of freedom
*If T test > T value, the difference between two means is statistically significant.
**If T test < T value, the difference between two means is not statistically significant.

As concluded in Table 18, 19, 20, 21, and 22, there was a significant difference between the ratio of tRNA/rRNA for experimental group (19R/PTZ+ positive extract) in comparison with control group (19R/PTZ+10% DMSO). In other words, in the presence of active extracts the level of ribosomal RNA (rRNA) decreased. This reduction could be caused by non-functional RNaseP, since precursor rRNA is a substrate for RNaseP holoenzyme. However, this reduction was not observed on cells bearing rnpB (M1RNA) gene cloned on a high copy plasmid. Because excess of M1RNA increases the formation of functional RNaseP which supports cell growth.

Discussion. Bacterial strains have become resistant to numerous available antibiotics. Most new antibiotics exert their action on classic targets such as protein synthesis and cell wall formation. The work described here attempted to identify new antimicrobials with novel specificity and mode of action from a library of plant extracts. In this study RNaseP assembly was the focus as a new antibacterial target.

The assay utilized two matched strains of *E. coli*. The first strain (DM46) contains the RNaseP RNA gene (rnpB) cloned on a high-copy plasmid. The second strain (19R/PTZ) contains the vector plasmid, but only a chromosomal copy of rnpB. While not wishing to be bound by theory, it was hypothesized that overexpressing the RNA component of RNaseP from the multicopy plasmid can suppress the inhibitory effect of these extracts by driving the assembly equilibrium toward making enough RNaseP for cell survival. The stiochiometry of subunits in the holoenzyme is 1:1 (Viogue, et al., 1988). Furthermore, the assembly of complex is irreversible.

Potential antimicrobials were identified from a library of 700 plant extracts by their ability to inhibit the growth of strain 19R/PTZ, but not strain DM46.

While not wishing to be bound by theory, it is contemplated that the assembly of RNaseP in strain DM46 is favored by excess synthesis of RNaseP RNA, compounds that inhibit the growth of 19R/PTZ, but not DM46 could be inhibitors of RNaseP assembly. The high-throughput microbiological screening assay was used to identify inhibitors of bacterial growth.

From a library of 700 plant extracts, 14 were screened as initial positive extracts. Further analysis indicated that these positive extracts could be divided into two groups, based upon their inhibitory characteristics. Group one inhibited the growth of only 19R/PTZ strains, whereas group two inhibited the growth of both 19R/PTZ and DM46 strains, although the latter strain was less sensitive to inhibition.

The inhibitory characteristic of B855575-4 may be found in the following steps:
1. Transcription of protein subunit (C5);
2. Translation of C5;
3. Transcription of RNA moiety of RNaseP holoenzyme (M1RNA);
4. Processing of M1RNA;
5. Transcription and processing of the RNA;
6. Transcription and translation of the RNA;
7. Assembly of two subunits (C5 and M1RNA);
8. Targeting of complex (RNaseP) to the membrane.

Any of the above steps could be targeted by our inhibitor B855575-4.

Example 2

Screening Assay. Using the growth assay system described above 700 plant extracts derived from the National Cancer Institute collection were screened for their effect on bacterial cell growth. The assay was carried out as a two-step process. First compounds were screened against the control strain, DM100 (Daniel P. Morse, Ph.D. dissertation, University of Missouri, 1991). Extracts which inhibited the control strain were then tested against the DM46 (Daniel P. Morse, Ph.D. dissertation, University of Missouri, 1991) strain containing multicopy rnpB. This two step process determined whether the hits were due to selective inhibition, as opposed to general cytotoxicity.

The initial hit rate was 0.5-1%.

Example 3

Screening Against Gram-positive Organisms. Many important pathogens are members of the phylogenetically distinct Gram-positive bacteria. Although it can be possible to identify lead extracts that are active against Gram-positives (see Table No. 24, below), this cannot be guaranteed, nor can the use of *E. coli* as the indicator organism detect those targets which are unique to these organisms. Accordingly, screening will be done against *Bacillus subtilis* as the indicator organism.

Library Construction. A number of *Bacillus* multi-copy plasmids are available (see, for example, Bron S. 1990. Plasmids. In C. R. Harwood and S. M. Cutting eds. Molecular Biological Methods For *Bacillus*. New York, Wiley), but illustratively plasmid pHV1432 (Janniere L et al., 1990. Gene 87:53-61) was chosen for this example. Replication proceeds via a theta-type mechanism which confers superior stability to those vectors that replicate via a ssDNA intermediate such as pE194 and pUB110. Plasmid pHV1432 has several unique restriction sites, the pBR322 plasmid origin for efficient library construction in *E. coli*, and can be used to maintain insert sizes of greater than 20 kb. The estimated copy number of this plasmid in *B. subtilis* is 200. For library construction, multiple *E. coli* strains are available. Strain DH10B (Gibco/Life Technologies) will be used, as it can be transformed at very high frequencies. Commercially available cells exhibit transformation frequencies greater than $1\times10^{10}/\mu g$. This *E. coli* strain lacks several restriction systems and has a mutated endA gene thus increasing library representation and plasmid quality, respectively. The *Bacillus subtilis* strain 6GM (BGSC 1A685) will be used as host, since it is restriction deficient (thus facilitating transformation of DNA derived from *E. coli*, (see, Haima P, et al., 1987. Mol. Gen. Genet. 209:335-342)) and competent cells of this strain are highly transformable.

A modification of the Xho I half site fill in strategy will be employed to maximize the number of plasmids that (a) contain inserts and (b) do not contain multiple inserts. Briefly, plasmid pHV1432 will be linearized by digestion with the restriction endonuclease SalI, which cuts once within the tetracycline (Tc) resistance gene. Following digestion the vector is incubated with the Klenow fragment of DNA polymerase I in the presence of dCTP and dTTP. This results in a linearized vector with a 5' CT overhang at each end. The *Bacillus subtilis* DNA (prepared by standard methods) will be partially digested with Sau 3A1, treated with the Klenow fragment of DNA polymerase I in the presence of dATP and dGTP (yielding DNA molecules with 5' GA overhangs). Genomic DNA fragments in the 3-5 kb size range will be separated by agarose gel electrophoresis, excised and purified using the Qiagen® gel extraction kit. This fill in strategy prevents vector religation and eliminates insert concatamerization or circularization. Following ligation (3:1 molar ratio of insert:vector) at 16° C., the ligation mixture will be used to transform *E. coli* DH10B to chloramphenicol (Cm) resistance. Transformants will be pooled in batches of approximately 1000 and stored in glycerol at −80° C. The number of transformants that contain inserts can be assessed by comparing the number of transformants from a "vector-alone" ligation, by determining the proportion of Cm resistant cells that are Tc sensitive, or by a quick miniprep screen of 20-30 transformants.

Plasmid DNA will be extracted from each sub-library pool, using a commercially available kit (see, for example, Qiagen®). *B. subtilis* competent cells will be prepared according to standard published methods (see, for example, Anagnostopoulis C. and Spizizen J., 1961. J. Bacteriol. 81:741-746). Transformation frequencies in excess of $10^4$ per microgram (the frequency for direct cloning in *B. subtilis*) are anticipated. It should be pointed out that although efficient DNA uptake by *B. subtilis* competent cells requires multimeric DNA, a sufficient quantity of plasmid multimers is present in plasmid preparations from *E. coli*. The resulting *B. subtilis* transformants will be plated on media containing chloramphenicol (the resistance gene expressed in *B. subtilis*). Pools of *B. subtilis* transformants will be harvested and stored at −80° C.

Example 4

Determination of Minimum Inhibitory Concentration. Indicator bacteria or fungi are grown either as a lawn on Petri plates supplemented with medium that allows growth of the indicator strain by standard microbiological technique. Serial dilutions of the antimicrobial agent are applied to the plate, either directly, or pre-adsorbed onto sterile filter paper discs (for example, BBL Microbiology Systems, Cockeysville, Md. 21030 catalogue no. 31039). The lowest concentration that results in a visible zone of inhibition is determined to be the Minimal Inhibitory Concentration. Alternatively, antimicrobial agents may be diluted in liquid culture medium suitable for the growth of the microbe. The liquid cultures are grown until a discernible difference in growth (for example, the optical density of the culture to light whose wavelength is 650 nanometers) is observed between the culture containing only solvent and the lowest concentration of the antimicrobial agent. In either case the Minimal Inhibitory Concentration is the lowest concentration of the antimicrobial agent that inhibits growth of the bacteria.

Example 5

The A49 mutant strain of *E. coli* (rnpA 49) is temperature-sensitive for the synthesis of tRNA and has lowered levels of ribonuclease P activity than does its wild-type, precursor (Schedl P. et al., 1975. Brookhaven Symposia in Biology: 53-76). The mutation is a missense, Arg to His, at position 38 in the sequence of the protein subunit of ribonuclease P. The physiological effect of the mutation is somewhat paradoxical. Although reduced in an amount relative to that found in the wild-type strain, purified ribonuclease P holoenzyme from the mutant strain is not itself temperature-sensitive and is kinetically similar to wild-type ribonuclease P. Rather than affecting activity, the rnpA 49 mutation affects assembly of the enzyme at high temperature. The rnpA 49 protein subunit has a lower affinity for its cognate RNA than does the wild type protein. Under nonpermissive conditions, the enzyme fails to assemble. Any preexisting activity is diluted over a few generations, leading to the cessation of cell growth.

When plasmid libraries of *E. coli* or other bacterial DNA are transformed into the A49 mutant strain, the cells that grow at 42° C. are transformed with one of two sequences. The first is rnpA (the parent mutation encoding the protein subunit), but the second is rnpB, the gene for the RNA component of the enzyme. Either sequence restores tRNA biosynthesis to a level compatible with growth, although the former is more effective. Relief of temperature-sensitivity by cloned rnpA sequences is easily rationalized since the sequences are homologous, but the basis for the ability of cloned sequences for the RNA component is less clear. Physiological and biochemical data indicate that the large excess of ribonuclease P RNA synthesized from the strong, high-copy promoter drives assembly of the holoenzyme by mass action. The overall phenomenon of relief of a mutation by overproduction of an interacting component is termed multicopy suppression. Multicopy suppression of rnpA by clones containing rnpB gene is more sensitive than its ability to confer growth on a strain deleted for the rnpB sequence. For example, all the transition mutants in rnpB that were isolated on the basis of their ability to suppress the rnpA 49 mutation were able to support growth of the strain whose chromosomal copy of ribonuclease P RNA was deleted. While not wishing to be bound by theory, it is contemplated that the weak binding of the mutant A49 protein sensitizes the system so that the native RNA structure is required for growth under nonpermissive conditions.

Example 6

Secondary Screening. The natural product extracts will be screened in the primary assay and those extracts found to contain putative inhibitors will be tested for their antimicrobial activity again versus an isogenic strain that produces ribonuclease P RNA at a higher level, as noted above. Those extracts demonstrating a good differential inhibition (from 2-to 30-fold for example) will be the lead extracts for fractionation. It is anticipated that about 1% of all extracts are potently inhibitory to the strain producing low levels of RNase P RNA and much less inhibitory to the high copy number strain. If the hit rate is much higher, to reduce the number of potential extracts for fractionation, at least one secondary discriminator to permit selection among the lead extracts can be established. This could be the use of a cytotoxicity assay in human cell lines, although it must be appreciated that extracts containing authentic inhibitors of ribonuclease P assembly could be screened out by virtue of the fact that they also contain structurally unrelated principles that adventitiously inhibit the growth of the human cells. High priority extracts for fractionation should also have the property that they display inhibitory activity toward a spectrum of clinically relevant bacteria (for example, *Staphylococcus* and *Pseudomonas*). The primary assay system will be used to guide the fractionation of the prioritized extracts to afford the putative active principles, and the differential inhibition against a strain that expresses ribonuclease P RNA at a higher level is maintained.

The extracts that are identified by the initial screening will be entered into a relational database along with data on their apparent minimum inhibitory concentration, spectrum of action and taxonomic source. The most promising extracts for further development into potential drug candidates will be, for example, those with the lowest minimum inhibitory concentration, broadest spectrum of action, and/or whose close taxonomic relatives also yield inhibitory extracts.

Example 7

Verification of Molecular Mechanism. The characterization of the molecular mechanism of the compounds will involve three complementary approaches: measurement of the effect of the compounds on in vitro reconstitution of ribonuclease P from its protein and RNA components, measurement of the physiological effect of the compounds on tRNA biosynthesis, and target identification by mutational analysis.

(i) In vitro reconstitution. Ribonuclease P in *E. coli* is composed of a protein subunit, termed C5, and an RNA, termed M1 (alternative nomenclature: P-protein and P-RNA). The enzyme self-assembles in vitro into a form containing two molecules of each subunit (1. Fang X W. Yang X J. Littrell K. Niranjanakumari S. Thiyagarajan P. Fierke C A. Sosnick T R. Pan T.). The *Bacillus subtilis* RNase P holoenzyme contains two RNase P RNA and two RNase P protein Subunits. RNA-A Publication of the RNA Society. 7 (2):233-41, 2001 February.

2. Loria A. Niranjanakumari S. Fierke C A. Pan T. Recognition of a pre-tRNA substrate by the *Bacillus subtilis* RNase P holoenzyme. Biochemistry. 37(44):15466-73, 1998 Nov. 3.). While the RNA itself is catalytically active, this activity depends on the presence of high counterion and $Mg^{2+}$ concentrations. Thus, under physiologically relevant salt conditions, the enzymatic activity of ribonuclease P depends on the amount of protein subunit.

Utilizing this dependence, the compounds will be tested to determine whether the compounds identified affect protein-RNA interaction. Briefly, M1 RNA will be incubated with limiting amounts of C5 protein in the presence of the compounds identify through screening. Then the initial velocity of substrate cleavage will be determined. Interference with association of the subunits will be indicated by a dose-dependent reduction in the initial velocity of the ribonuclease P reaction. Positive results will be checked by repeating the experiment in the presence of limiting RNA. The dependence of inhibition will be determined as a function of inhibitor concentration and the data used to determine the apparent inhibition constant of the inhibitor on assembly.

Negative results in this experiment do not preclude an effect of the compound on assembly in vivo. Assembly of the membrane-bound ribonuclease P involves a number of steps that are not yet determined, for example, specific transcriptional or translational events, targeting of the enzyme to the membrane, etc. It will most likely be necessary to confirm and/or extend these results by biological experiments.

(ii) Physiological measurements. To measure the effects of the compounds on tRNA biosynthesis in vivo by specific labeling experiments, first, the kinetics of the compounds' effect on cell growth will be determined. In positive extracts, the extracts do not arrest growth immediately, rather, cell growth continues for about 2 generations after treatment with extract. This is consistent with the hypothesis that the extracts target an assembly event, since pre-assembled ribonuclease P will be sufficient to support growth until it, and consequently, the pool of previously synthesized tRNAs is diluted below a critical level. (This behavior is exhibited by the rnpA 49 strains as well, since the mutation affects assembly of the enzyme rather than the activity of the pre-assembled enzyme.)

Whole cells, treated with inhibitor, will be labeled with [$^{32}$P] phosphate and small RNAs will be released by direct phenol treatment of the culture. After ethanol-precipitation and DNase treatment, small RNAs will be separated on 6% polyacrylamide gels and the amount of newly synthesized tRNA will be determined by phosphorimaging. An alternative, more sensitive assay of tRNA biosynthesis is to infect the treated cells with phage T4. The chief advantage of this experimental protocol is that T4 turns off host transcription and synthesizes a limited set of tRNAs, whose biosynthesis is nonetheless dependent on ribonuclease P.

(iii) Target identification by mutational analysis. To determine the components that may be affected by the compounds a mutant plasmid-free bacteria that are resistant to the inhibitors will be selected. It is contemplated that these mutations will be dominant and chromosomally encoded. The DNA will be cloned from these resistant strains into the low-copy vector pCL1921 and determine the identity of the inserts by sequencing them and mapping the sequences to the E. coli genomic sequence. It is contemplated that cloning resistant mutations into a low-copy vector will be necessary because the wild-type rnpB gene is known to cause resistance in high-copy.

It is contemplated that at least some of the genes encoding resistance will map to known components of ribonuclease P, that is, the protein or RNA subunits. It is also contemplated that these experiments will allow the identification of other components in the assembly pathway.

Example 8

Structural Modification of 3-O-Galloylshikimic Acid. To produce compounds with a broad range of antimicrobial activity and optimized for preclinical and clinical development, compounds identified as lead structures, for example, 3-O-galloylshikimic acid, will be structurally modified. In this fashion, other types of inhibitors may be identified.

Example 9

Characterization of Compounds for Their Activity Against Clinical Isolates. The growth assay as described above will be used to evaluate efficiency of plating measurements of clinical isolates for initial evaluation of potential clinical efficacy of the compounds isolated Clinical isolates were obtained from the University of Missouri Hospitals and Clinics, and include those listed in Table No. 23, below.

TABLE NO 23

| Clinical isolates | | |
|---|---|---|
| Strain | Source | Note |
| Haemophilus influenzae | A. L. Smith, M.D. | Otitis media patients |
| Neisseria meningitis | A. L. Smith, M.D. | Nonpathogenic BL2 strain |
| Pseudomonas aeruginosa | A. L. Smith, M.D., and D. Chance, Ph.D. | Cystic Fibrosis patients |
| Mycobacterium phlei | F. Schmidt, Ph.D. | ATCC strain |
| Staphylococcus aureus | A. L. Smith, M.D. | 138 clinical samples |

The activities of three active extracts against E. coli and against clinical isolates of S. aureus and P. aeruginosa are shown in Table No. 24, below. The minimum inhibitory concentration values were determined in liquid culture as described in above. At these concentrations, the efficiency of plating of the tested strains was <10$^{-4}$; values on plates were about 5-10 fold higher.

TABLE NO 24

| Minimum Inhibitory Concentrations or Three Active Extracts | | | |
|---|---|---|---|
| Extract | vs. Escherichia coli | vs. Staphylococcus aurenus | vs. Peudomonas aeruginosa |
| B855575-4 | 25 µg mL$^{-1}$ | not inhibitory | 25 µg mL$^{-1}$ |
| B855548-4 | 50 µg mL$^{-1}$ | 50 µg mL$^{-1}$ | 50 µg mL$^{-1}$ |
| B855205-4 | 50 µg mL$^{-1}$ | 50 µg mL$^{-1}$ | 25 µg mL$^{-1}$ |

Illustratively, if it is assumed that about 100 compounds are present in each extract, then the active principle is present at approximately 0.5 µg mL$^{-1}$. Again, assuming that the molecular weight of each of the active principles is roughly 400, and that each extract contains 100 or so separate compounds, the lead compounds are active at a concentration near 0.5-1.0 µM.

Example 10

Initiate Preclinical Characterization of Optimized Inhibitors. Cytotoxic compounds will be eliminated by screening the putative inhibitors of the ribonuclease P assembly as cytotoxins in representative human cell lines (for example, 3T6 cells) using standard cell culture techniques. Those compounds that do not show toxicity and that are candidates for further development will be tested for stability and acute toxicity in mice.

The contents of all cited references throughout this application are hereby expressly incorporated by reference. The practice of the present invention will employ, unless otherwise indicated, conventional techniques of pharmacology and pharmaceutics, which are within the skill of the art.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

The invention claimed is:

1. A method for identifying a gram-negative or gram-positive bacterial-inhibiting agent that selectively interrupts assembly of a predetermined biological process, comprising:
(a) contacting a genetically engineered host cell with the bacterial-inhibiting agent for a predetermined amount of time, wherein the host cell contains a bacterial DNA sequence encoding a protein of the predetermined biological process operatively associated with a regulatory DNA sequence that controls expression of said protein, so that the protein is stably expressed by the host cell;
(b) measuring growth of the host cell of (a);
(c) contacting a genetically engineered host cell with the bacteria-inhibiting agent for a predetermined amount of time, wherein the host cell contains multiple copies of the bacterial DNA sequence encoding the same protein of the predetermined biological process disclosed in (a) operatively associated with a regulatory DNA sequence that controls expression of said protein, so that the protein are stably expressed by the host cell;
(d) measuring growth of the host cell of (c);
(e) comparing the growth of the host cell of (a) with the growth of the host cell of (c); and
(f) identifying the bacterial-inhibiting agent that inhibits the growth of the host cell of (a) and does not inhibit the growth of the host cell of (c);
wherein the protein of the predetermined biological process is selected from the group consisting of: N-formylmethionyl-tRNA deformylase, ribosome-binding factor A, translation elongation factor Ts, translation initiation factor IF3, tRNA-(guanine-N1) methyltransferase, transcription elongation factor, ATPase involved in DNA replication initiation, DNA primase, DNA-dependent DNA polymerase III alpha chain, excinuclease ATPase subunit, helicase subunit of the DNA excision repair complex, helicase subunit of the Holliday junction resolvase (RuvB), Holliday junction DNA helicase subunit, NAD-dependent DNA ligase (BRCT domain type II), nuclease subunit of the excinuclease complex, ribonuclease P protein component, replicative DNA helicase, FKBP-type peptidyl-prolyl cis-trans isomerase (trigger factor), tmRNA-binding protein SmpB, predicted S-adenosyl-methionine-dependent methyltransferase involved in cell envelope biogenesis, prolipoprotein diacylglyceryltransferase, lipoprotein signal peptidase, preprotein translocase subunit SecA (ATPase, RNA helicase), preprotein translocase subunit SecE, ABC-type (unclassified) transport system, ATPase component, predicted methyltransferases, and uncharacterized BCR (putative metal-binding protein).

2. A method for identifying in a test sample an unknown gram-positive or gram-negative bacterial-inhibiting agent that interrupts assembly of a predetermined biological process, comprising:
(a) contacting a host bacterial strain with the test sample, wherein the bacteria strain contains a gene for the assembly of the predetermined biological process that is conserved in bacteria;
(b) incubating the bacterial strain of (a) in presence of the test sample for a predetermined amount of time;
(c) measuring bacterial growth of the bacterial strain of (a);
(d) contacting a host bacterial strain containing multiple copies of the same gene disclosed in (a) with the test sample;
(e) incubating the bacterial strain of (d) in presence of the test sample for a predetermined amount of time;
(f) measuring bacterial growth of the bacterial strain of (d); and
(g) identifying the test sample that inhibits the growth of the bacterial strain of (a) and does not inhibit the growth of the bacterial strain of (d);
wherein the gene for the assembly of the predetermined biological process is selected from the group consisting of: N-formylmethionyl-tRNA deformylase, ribosome-binding factor A, translation elongation factor Ts, translation initiation factor IF3, tRNA-(guanine-N1) methyltransferase, transcription elongation factor, ATPase involved in DNA replication initiation, DNA primase, DNA-dependent DNA polymerase III alpha chain, excinuclease ATPase subunit, helicase subunit of the DNA excision repair complex, helicase subunit of the Holliday junction resolvase (RuvB), Holliday junction DNA helicase subunit, NAD-dependent DNA ligase (BRCT domain type II), nuclease subunit of the excinuclease complex, ribonuclease P protein component, replicative DNA helicase, FKBP-type peptidyl-prolyl cis-trans isomerase (trigger factor), tmRNA-binding protein SmpB, predicted S-adenosylmethionine-dependent methyltransferase involved in cell envelope biogenesis, prolipoprotein diacylglyceryltransferase, lipoprotein signal peptidase, preprotein translocase subunit SecA (ATPase, RNA helicase), preprotein translocase subunit SecE, ABC-type (unclassified) transport system, ATPase component, predicted methyltransferases, and uncharacterized BCR (putative metal-binding protein).

3. The method of claim 2, wherein the bacterial strain of (a) and (d) comprises a gene for the assembly of bacterial ribonuclease P.

4. The method of claim 2, wherein the bacterial strain of (a) is E. coli strain DM100 comprising a single copy of SEQ ID NO:1.

5. The method of claim 2, wherein the bacterial strain of (d) is E. coli strain DM46 comprising multiple copies of SEQ ID NO:1.

6. The method of claim 2, wherein the bacterial growth is measured by optical density.

7. The method of claim 2, wherein the bacterial growth is measured by optical density of a pH-indicator dye.

8. The method of claim 7, wherein the pH-indicator dye is phenol red.

9. The method of claim 8, wherein the optical density is measured using dual reading wavelengths of about 570 nm against a about 640 nm reference.

10. The method of claim 2, further comprising fractionating the test sample identified in (g) and re-testing each fraction according to steps (a) through (g) to identify the fraction that inhibits the growth of the bacterial strain of (a) and does not inhibit the growth of the bacterial strain of (d).

11. The method of claim 10, wherein the fractionation step is by a polyamide 6S column.

12. The method of claim 10, wherein the fractionation step is by a HP20SS column.

13. The method of claim 10, wherein the fractionation step is by a $C_{18}$ reversed phase HPLC column.

14. The method of claim 1 or 2, wherein the bacterial-inhibiting agent interrupts ribonuclease P in E. coli.

15. The method of claim 1 or 2, wherein the predetermined amount of time is selected from the group consisting of: 4, 6, 8, 12, 24, or 48 hours.

16. The method of claim 1 or 2, wherein the predetermined amount of time is overnight.

17. A method for identifying a gram-negative or gram-positive bacterial-inhibiting agent that selectively interrupts assembly of bacterial ribonuclease P, comprising:
  (a) contacting a genetically engineered host cell with the bacterial-inhibiting agent for a predetermined amount of time, wherein the host cell contains a bacterial DNA sequence encoding bacterial ribonuclease P operatively associated with a regulatory DNA sequence that controls expression of said bacterial ribonuclease P, so that the bacterial ribonuclease P is stably expressed by the host cell;
  (b) measuring growth of the host cell of (a);
  (c) contacting a genetically engineered host cell with the bacteria-inhibiting agent for a predetermined amount of time, wherein the host cell contains multiple copies of the bacterial DNA sequence encoding the same bacterial ribonuclease P disclosed in (a) operatively associated with a regulatory DNA sequence that controls expression of said bacterial ribonuclease P, so that the bacterial ribonuclease P is stably expressed by the host cell;
  (d) measuring growth of the host cell of (c);
  (e) comparing the growth of the host cell of (a) with the growth of the host cell of (c); and
  (f) identifying the bacterial-inhibiting agent that inhibits the growth of the host cell of (a) and does not inhibit the growth of the host cell of (c);
wherein the host cell is selected from the group consisting of E. coli and B. subtilis.

18. The method of claim 17, wherein the E. coli host cell of (a) is E. coli strain DM100 comprising a single copy of SEQ ID NO:1.

19. The method of claim 17, wherein the E. coli host cell of (c) is E. coli strain DM46 comprising multiple copies of SEQ ID NO:1.

20. A method for identifying in a test sample an unknown gram-positive or gram-negative bacterial-inhibiting agent that interrupts assembly of bacterial ribonuclease P, comprising:
  (a) contacting a host bacterial strain with the test sample, wherein the bacteria strain contains a gene for the assembly of bacterial ribonuclease P that is conserved in bacteria;
  (b) incubating the bacterial strain of (a) in presence of the test sample for a predetermined amount of time;
  (c) measuring bacterial growth of the bacterial strain of (a);
  (d) contacting a host bacterial strain containing multiple copies of the same gene disclosed in (a) with the test sample;
  (e) incubating the bacterial strain of (d) in presence of the test sample for a predetermined amount of time;
  (f) measuring bacterial growth of the bacterial strain of (d); and
  (g) identifying the test sample that inhibits the growth of the bacterial strain of (a) and does not inhibit the growth of the bacterial strain of (d);
wherein the host bacterial strain is selected from a group consisting of E. coli and B. subtilis.

21. The method of claim 20, wherein the E. coli bacterial strain of (a) is E. coli strain DM100 comprising a single copy of SEQ ID NO:1.

22. The method of claim 20, wherein the E. coli bacterial strain of (d) is E. coli strain DM46 comprising multiple copies of SEQ ID NO:1.

23. The method of claim 17 or 20, wherein the predetermined amount of time is selected from the group consisting of: 4, 6, 8, 12, 24, or 48 hours.

24. The method of claim 17 or 20, wherein the predetermined amount of time is overnight.

* * * * *

SEQUENCE LISTING

<160> NUMBER OF SEQ ID NOS: 1

<210> SEQ ID NO 1
<211> LENGTH: 377
<212> TYPE: DNA
<213> ORGANISM: Escherichia coli

<400> SEQUENCE: 1

```
gaagctgacc agacagtcgc cgcttcgtcg tcgtcctctt cggggagac gggcggaggg      60 gaggaaagtc cgggctccat agggcagggt gccaggtaac gcctgggggg gaaacccacg     120
accagtgcaa cagagagcaa accgccgatg gcccgcgcaa gcgggatcag gtaagggtga    180
aagggtgcgg taagagcgca ccgcgcggct ggtaacagtc cgtggcacgg taaactccac    240
ccggagcaag gccaaatagg ggttcataag gtacggcccg tactgaaccc gggtaggctg    300
cttgagccag tgagcgattg ctggcctaga tgaatgactg tccacgacag aacccggctt    360
atcggtcagt ttcacct                                                   377
```